United States Patent
Moss et al.

(10) Patent No.: US 7,211,575 B2
(45) Date of Patent: May 1, 2007

(54) METHODS OF TREATING CYTOKINE MEDIATED DISEASES

(75) Inventors: Neil Moss, Ridgefield, CT (US); John Robinson Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 992 days.

(21) Appl. No.: 10/237,306

(22) Filed: Sep. 9, 2002

(65) Prior Publication Data

US 2003/0060455 A1    Mar. 27, 2003

Related U.S. Application Data

(60) Provisional application No. 60/318,958, filed on Sep. 13, 2001.

(51) Int. Cl.
*A61K 31/54*    (2006.01)
(52) U.S. Cl. .................................. 514/227.8
(58) Field of Classification Search .............. 514/227
See application file for complete search history.

(56) References Cited

U.S. PATENT DOCUMENTS

| | | | |
|---|---|---|---|
| 6,319,921 B1 * | 11/2001 | Cirillo et al. ............ | 514/236.5 |
| 6,358,945 B1 * | 3/2002 | Breitfelder et al. ...... | 514/227.8 |
| 6,608,052 B2 * | 8/2003 | Breitfelder et al. ...... | 514/227.8 |
| 6,720,321 B2 * | 4/2004 | Cirillo et al. ............ | 514/235.8 |

FOREIGN PATENT DOCUMENTS

| WO | WO 99/23091 | 5/1999 |
|---|---|---|
| WO | WO 00/41698 | 7/2000 |
| WO | WO 00/55139 | 9/2000 |

* cited by examiner

*Primary Examiner*—Thurman K. Page
*Assistant Examiner*—Sudhakar Katakam
(74) *Attorney, Agent, or Firm*—Michael Morris; Mary-Ellen M. Devlin; Anthony P. Bottino

(57) ABSTRACT

Disclosed are methods of treating acute and chronic inflammation in the lung caused by inhalation of smoke, endometriosis, Behcet's disease, uveitis, ankylosing spondylitis, pancreatitis, cancer, Lyme disease, sepsis, chronic obstructive pulmonary disease, traumatic arthritis, congestive heart failure and restenosis following percutaneous transluminal coronary angioplasty, known to be cytokine mediated, using aromatic heterocyclic compounds described in WO 00/55139.

11 Claims, No Drawings

METHODS OF TREATING CYTOKINE MEDIATED DISEASES

APPLICATION DATA

This application claims benefit to U.S. provisional application Ser. No. 60/318,958 filed Sep. 13, 2001.

TECHNICAL FIELD OF THE INVENTION

This invention relates to methods of treating acute and chronic inflammation in the lung caused by inhalation of smoke, endometriosis, Behcet's disease, uveitis, ankylosing spondylitis, pancreatitis, cancer, Lyme disease, percutaneous transluminal coronary angioplasty, Alzheimer's disease, traumatic arthritis, sepsis, chronic obstructive pulmonary disease and congestive heart failure indicated to be cytokine mediated diseases using aromatic heterocyclic compounds disclosed in PCT publication WO 00/55139.

BACKGROUND OF THE INVENTION

In WO 00/55139 there are described aromatic heterocyclic compounds useful in treating certain cytokine mediated diseases. Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in the pathogenesis of restenosis after percutaneous transluminal coronary angioplasty (PTCA) (Tashiro, H., et al., March 2001, *Coron Artery Dis* 12(2): 107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3–12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.,* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia.

Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNF anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res May 15, 2000 90(2)95–101; Shock September 1998 10(3):160–75. p38MAPkinase pathway plays an role in B.burgdorferi-elicited infammation and may be useful in treating inflammation induced by the Lyme disease agent. Anguita, J. et. al., *The Journal of Immunology,* 2002,168:6352–6357.

Anti-cytokine drugs may also have therapeutic utility in treating tumor cells. Drug Resistance Updates 4(4):253–267, August 2001 WO 02/38143 discloses the use of p38 inhibitors to enhance the efficacy and safety of genotoxic therapy for treating, for example, aging, cancer and certain types of heart failure.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure. None of these specific diseases have been taught or described in WO 00/55139 as being possible indications for the compounds taught therein. Therefore a need exists for small molecule inhibitors for treating these diseases with optimized efficacy, pharmacokinetic and safety profiles.

BRIEF SUMMARY OF THE INVENTION

The present invention is directed a method of treating a cytokine mediated disease or condition chosen from: acute and chronic inflammation in the lung caused by inhalation of smoke, endometriosis, Behcet's disease, uveitis, ankylosing spondylitis, pancreatitis, cancer, Lyme Disease, restenosis following percutaneous transluminal coronary angioplasty, Alzheimer's disease, traumatic arthritis, sepsis, chronic obstructive pulmonary disease and congestive heart failure, said method comprising administering to a patient in need of such treatment a therapeutically effective amount of compounds disclosed in in WO 00/55139.

DETAILED DESCRIPTION OF THE INVENTION

In a first broad generic aspect, the present invention is directed a method of treating a cytokine mediated disease or condition chosen from: acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure, said method comprising administering to a patient in need of such treatment a therapeutically effective amount of a compound of the formula (I) disclosed in WO 00/55139 which is the PCT case of U.S. application Ser. No. 09/505,582 (both of which are incorporated by reference herein in it their entirety):

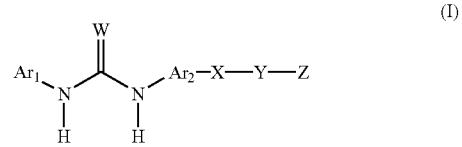

wherein:
Ar$_1$ is selected from the group consisting of:
pyrrole, pyrrolidine, pyrazole, imidazole, oxazole, thiazole, furan and thiophene; wherein Ar$_1$ may be substituted by one or more R$_1$, R$_2$ or R$_3$;
Ar$_2$ is:
phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with zero to three R$_2$ groups;
X is:
a) a C$_{5-8}$ cycloalkyl or cycloalkenyl optionally substituted with 0–2 oxo groups or 0–3 C$_{1-4}$ branched or unbranched alkyl, C$_{1-4}$ alkoxy or C$_{1-4}$ alkylamino chains;
b) phenyl, furan, thiophene, pyrrole, imidazolyl, pyridine, pyrimidine, pyridinone, dihydropyridinone, maleimide, dihydromaleimide, piperdine, piperazine or pyrazine each being optionally independently substituted with 0–3 C$_{1-4}$ branched or unbranched alkyl, C$_{1-4}$ alkoxy, hydroxy, nitrile, mono- or di-(C$_{1-3}$ alkyl)amino, C$_{1-6}$ alkyl-S(O)$_m$, or halogen;
Y is:
a bond or a C$_{1-4}$ saturated or unsaturated branched or unbranched carbon chain optionally partially or fully halogenated, wherein one or more methylene groups are optionally replaced by O, NH, S(O), S(O)$_2$ or S and wherein Y is optionally independently substituted with 0–2 oxo groups and one or more C$_{1-4}$ branched or unbranched alkyl which may be substituted by one or more halogen atoms;
Z is:
a) phenyl, pyridine, pyrimidine, pyridazine, imidazole, furan, thiophene, pyran, which are optionally substituted with one to three groups consisting of halogen, C$_{1-6}$ alkyl, C$_{1-6}$ alkoxy, hydroxy, mono- or di-(C$_{1-3}$ alkyl)amino, C$_{1-6}$ alkyl-S(O)$_m$, COOH and phenylamino wherein the phenyl ring is optionally substituted with one to two groups consisting of halogen, C$_{1-6}$ alkyl and C$_{1-6}$ alkoxy;
b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, piperazine, tetrahydropyrimidone, cyclohexanone, cyclohexanol, pentamethylene sulfide, pentamethylene sulfoxide, pentamethylene sulfone, tetramethylene sulfide, tetramethylene sulfoxide or tetramethylene sulfone which are optionally substituted with one to three groups consisting of nitrile, C$_{1-6}$ alkyl, C$_{1-6}$ alkoxy, hydroxy, mono- or di-(C$_{1-3}$ alkyl)amino-C$_{1-3}$ alkyl, phenylamino-C$_{1-3}$ alkyl and C$_{1-3}$ alkoxy-C$_{1-3}$ alkyl;
c) C$_{1-6}$ alkoxy, secondary or tertiary amine wherein the amino nitrogen is covalently bonded to groups selected from the group consisting of C$_{1-3}$ alkyl, C$_{1-5}$ alkoxyalkyl, pyridinyl-C$_{1-3}$ alkyl, imidazolyl-C$_{1-3}$ alkyl, tetrahydrofuranyl-C$_{1-3}$ alkyl, phenylamino, wherein the phenyl ring is optionally substituted with one to two halogen, C$_{1-6}$ alkoxy, hydroxy or mono- or di-(C$_{1-3}$ alkyl)amino, C$_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;

$R_1$ is:
(a) $C_{3-10}$ branched or unbranched alkyl optionally partially or fully halogenated and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described in this paragraph, and being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$)alkylaminocarbonyl;
(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl each being optionally be partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;
(c) $C_{3-10}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di($C_{1-3}$)alkylaminocarbonyl;
(d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;
(e) nitrile; or
(f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:
a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;

$R_3$ is:
a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, nitrile, $C_{1-3}$ alkyloxy which may optionally be partially or fully halogenated, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-$C(O)$—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—$C(O)$—$C_{1-5}$ alkyl and $R_7$—$C_{1-5}$ alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-4}$ alkyl-$OC(O)$, $C_{1-5}$ alkyl-$C(O)$—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—$C(O)$—$C_{1-5}$ alkyl, and $R_{12}$—$C_{1-5}$ alkyl($R_{13}$)N;

c) cycloalkyl selected from the group consisting of cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, alkoxycarbonylalkyl or phenylsulfonyl; or f) $C_{1-6}$ branched or unbranched alkyl optionally partially or fully halogenated;

or $R_1$ and $R_2$ taken together may optionally form a fused phenyl or pyridinyl ring;

each $R_8$ and $R_{13}$ is independently selected from the group consisting of: hydrogen and $C_{1-4}$ branched or unbranched alkyl optionally be partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S and the pharmaceutically acceptable derivatives thereof.

A preferred subgeneric aspect of the invention comprises a method of using the compounds of the formula(I) as provided above and wherein:

$Ar_2$ is naphthyl, tetrahydronaphthyl, indanyl or indenyl and W is O.

A more preferred subgeneric aspect of the invention comprises a method of using the compounds of the formula (I) as provided above and wherein:

$Ar_1$ is selected from thiophene and pyrazole;

X is $C_{5-7}$ cycloalkyl or $C_{5-7}$ cycloalkenyl optionally substituted with 0–2 oxo groups or 0–3 $C_{1-4}$ branched or unbranched alkyl, $C_{1-4}$ alkoxy or $C_{1-4}$ alkylamino; or X is phenyl, pyridine, tetrahydropyridine, pyrimidine, furan or thiophene each being optionally independently substituted with 0–3 $C_{1-4}$ branched or unbranched alkyl, $C_{1-4}$ alkoxy, hydroxy, nitrile, mono- or di-($C_{1-3}$ alkyl)amino, $C_{1-6}$ alkyl-$S(O)_m$ or halogen;

$R_1$ is $C_{1-4}$ alkyl branched or unbranched, cyclopropyl or cyclohexyl optionally partially or fully halogenated and optionally substituted with one to three $C_{1-3}$ alkyl groups;

$R_3$ is $C_{1-4}$ alkyl branched or unbranched, phenyl, pyrimidinyl, pyrazolyl or pyridinyl each being optionally substituted as described hereinabove in the broadest generic aspect, alkoxycarbonylalkyl or cyclopropyl or cyclopentyl optionally substituted as described hereinabove in the broadest generic aspect.

A yet more preferred subgeneric aspect of the invention comprises a method of using the compounds of the formula (I), as described in the immediate previous paragraph, wherein:

$Ar_1$ is pyrazole;

X is cyclopentenyl, cyclohexenyl or cycloheptenyl, optionally substituted with an oxo group or 0–3 $C_{1-4}$ branched or unbranched alkyl, $C_{1-4}$ alkoxy or $C_{1-4}$ alkylamino; or X is phenyl, pyridine, furan or thiophene each being optionally independently substituted with 0–3 $C_{1-4}$ branched or unbranched alkyl, $C_{1-4}$ alkoxy, hydroxy, nitrile, mono- or di-($C_{1-3}$ alkyl)amino, $C_{1-6}$ alkyl-$S(O)_m$ or halogen.

A yet further preferred subgeneric aspect of the invention comprises a method of using the compounds of the formula (I), as described in the immediate previous paragraph, and wherein:

Y is —CH2-, —CH2CH2-, —CH2NH—, —CH2CH2NH— or a bond;

and

Z is phenyl, imidazole, furan, piperazine, tetrahydropyran, morpholine, thiomorpholine, thiomorpholine sulfoxide, piperidine, pyridine, secondary or tertiary amine wherein the amino nitrogen is covalently bonded to groups selected from the group consisting of $C_{1-3}$ alkyl and $C_{1-5}$ alkoxyalkyl, phenylamino wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$ and phenyl-$S(O)_m$ wherein the phenyl ring is optionally substituted with one to two halogen, $C_{1-6}$ alkoxy, hydroxy or mono- or di-($C_{1-3}$ alkyl)amino.

A further preferred subgeneric aspect of the invention comprises a method of using the compounds of the formula (I), as described in the immediate previous paragraph, and wherein:

$Ar_1$ is 5-tert-butyl-pyrazol-3-yl; wherein the pyrazole ring may be substituted by $R_3$;

$R_3$ is $C_{1-4}$ alkyl branched or unbranched, phenyl, pyrimidinyl, pyrazolyl, pyridinyl each being optionally substituted as described hereinabove in the broadest generic aspect, alkoxycarbonylalkyl or cyclopropyl or cyclopentyl optionally substituted as described hereinabove in the broadest generic aspect.

A still yet further preferred subgeneric aspect of the invention comprises a method of using the compounds of the formula (I), as described in the immediate previous paragraph, and wherein:

X is pyridinyl.

A still yet further preferred subgeneric aspect of the invention comprises a method of using the compounds of the formula (I), as described in the immediate previous paragraph, and wherein:

the pyridinyl is attached to $Ar_1$ via the 3-pyridinyl position.

The following compounds are representative of the compounds of formula(I) which may be useful in the novel methods described herein:

1-[5-tert-butyl-2-p-tolyl-2H-pyrazol-3-yl]-3-[4-(4-(morpholin-4-yl)phenyl)naphthalen-1-yl]urea;

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(4-dimethylaminophenyl)naphthalen-1-yl]urea;

1-[5-tert-butyl-2-p-tolyl-2H-pyrazol-3-yl]-3-[4-(3-(morpholin-4-yl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fur-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin -3-yl)naphthalen-1-yl]urea;

1-[5-tert-butyl-2-phenyl-2H-pyrazol-3-yl]-3-[4-(4-piperdin-1-ylmethyl-phenyl)naphthalen-1-yl]urea;

1-[5-tert-butyl-2-phenyl-2H-pyrazol-3-yl]-3-[4-(4-(4-methylpiperazin-1-yl)methylphenyl)naphthalen-1-yl]urea;

1-[5-tert-butyl-2-p-tolyl-2H-pyrazol-3-yl]-3-[4-(3,4-di(morpholin-4-yl-methyl)phenyl)naphthalen-1-yl]urea;

1-[5-tert-butyl-2-(6-methyl-pyridin-3-yl)-2H-pyrazol-3-yl]-3-[4-(6-pyridin-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-thiomorpholin-4-ylmethyl)pyridin-3-yl)naphthalen-1-yl]urea;

1-[5-tert-butyl-2-p-tolyl-2H-pyrazol-3-yl]-3-[4-(6-(1-oxo-thiomorpholin-4-ylmethyl)pyridin-3-yl)naphthalen-1-yl]urea;

1-[5-tert-butyl-2-(6-methyl-pyridin-3-yl)-2H-pyrazol-3-yl]-3-[4-(6-tetrahydropyran-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-tetrahydrothiophen-3-ylmethyl)pyridin-3-yl)naphthalen-1-yl]urea;

1-[5-tert-butyl-2-(6-methyl-pyridin-3-yl)-2H-pyrazol-3-yl]-3-[4-(6-(imidazol-1-ylmethyl)pyridin-3-yl)naphthalen-1-yl]urea;

1-[2-(3-dimethylaminomethylphenyl)-5-(1-methyl-cyclohexyl)-2H-pyrazol-3-yl]-3-[4-(6-morpholin-4-ylmethyl-pyridin-3-yl)naphthalen-1-yl]urea;

1-[2-(5-(1-methyl-cyclohexyl)-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(2-morpholin-4-ylmethyl-pyrimidin-5-yl)naphthalen-1-yl]urea;

1-[5-tert-butyl-2-(6-methyl-pyridin-3-yl)-2H-pyrazol-3-yl]-3-[4-(3-methoxy-5-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-(3-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-3-(dimethylamino)phenyl)naphthalen-1-yl]urea;

1-[5-tert-butyl-2-(6-methyl-pyridin-3-yl)-2H-pyrazol-3-yl]-3-[4-3-(methylsulfonyl)phenyl)naphthalen-1-yl]urea;

5-tert-butyl-3-{3-[4-(6-morpholin-4-ylmethyl-pyridin-3-yl)naphthalen-1-yl]ureido}thiophene-2-carboxylic acid methyl ester;

5-tert-butyl-3-{3-[4-(6-morpholin-4-ylmethyl-pyridin-3-yl)naphthalen-1-yl]ureido}thiophene-2-carboxylic acid methylamide;

5-tert-butyl-1-methyl-3-{3-[4-(6-morpholin-4-ylmethyl-pyridin-3-yl)naphthalen-1-yl]ureido}-1H-pyrrole-2-carboxylic acid methyl ester;

5-tert-butyl-1-methyl-3-{3-[4-(6-morpholin-4-ylmethyl-pyridin-3-yl)naphthalen-1-yl]ureido}-1H-pyrrole-2-carboxylic acid methylamide;

2-acetylamino N-(5-tert-butyl-3-{3-[4-(6-morpholin-4-ylmethyl-pyridin-3-yl)naphthalen-1-yl]ureido}thiophen-2-ylmethyl)acetamide;

1-[5-tert-butyl-2-p-tolyl-2H-pyrazol-3-yl]-3-[4-(3-morpholin-4-yl-cyclohex-1-enyl)naphthalen-1-yl]urea;

1-[5-tert-butyl-2-p-tolyl-2H-pyrazol-3-yl]-3-[4-(3-morpholin-4-yl-cylohept-1-enyl)naphthalen-1-yl]urea;

1-[5-tert-butyl-2-p-tolyl-2H-pyrazol-3-yl]-3-[4-(3-(2-morpholin-4-yl-ethylamino)cyclohex-1-enyl)naphthalen-1-yl]urea;

1-[5-tert-butyl-2-p-tolyl-2H-pyrazol-3-yl]-3-[4-(3-morpholin-4-yl-cyclohept-1-enyl)naphthalen-1-yl]urea;

1-[5-tert-butyl-2-(6-methyl-pyridin-3-yl)-2H-pyrazol-3-yl]-3-[4-(3-(pyridin-4-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(dimethylaminoethylamino)cyclohex-1-enyl)naphthalen-1-yl]urea;

1-[5-tert-butyl-2-(6-methyl-pyridin-3-yl)-2H-pyrazol-3-yl]-3-[4-(3-(pyridin-3-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(phenyl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-phenylethylamino)cyclohex-1-enyl)naphthalen-1-yl]urea;

1-[5-tert-butyl-2-(6-methyl-pyridin-3-yl)-2H-pyrazol-3-yl]-3-[4-(3-(furan-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-pyridin-2-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-piperdin-1-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-imidazol-4-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-pyridin-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-(4-methoxyphenyl)ethylamino)cyclohex-1-enyl)naphthalen-1-yl]urea;

1-[5-tert-butyl-2-p-tolyl-2H-pyrazol-3-yl]-3-[4-(4-morpholin-4-ylmethyl-3-oxo-cyclohex-1-enyl)naphthalen-1-yl]urea;

1-[5-tert-butyl-2-p-tolyl-2H-pyrazol-3-yl]-3-[4-(4-(1-oxo-tetrahydrothiophen-3-ylmethyl)-3-oxo-cyclohex-1-enyl)naphthalen-1-yl]urea;

1-[5-tert-butyl-2-p-tolyl-2H-pyrazol-3-yl]-3-[4-(4-(1-oxo-thiomorpholin-4-ylmethyl)-3-oxo-cyclohex-1-enyl)naphthalen-1-yl]urea;

1-[5-tert-butyl-2-p-tolyl-2H-pyrazol-3-yl]-3-[4-(4-(methylpiperazin-1-ylmethyl)-3-oxo-cyclohex-1-enyl)naphthalen-1-yl]urea;

1-[5-tert-butyl-2-(6-methyl-pyridin-3-yl)-2H-pyrazol-3-yl]-3-[4-{6-oxo-1-(tetrahydro-pyran-4-ylmethyl)-1,2,3,6-tetrahydro-pyridin-4-yl}naphthalen-1-yl]urea;

1-[5-tert-butyl-2-(6-methyl-pyridin-3-yl)-2H-pyrazol-3-yl]-3-[4-(2-oxo-1-pyridin-4-ylmethyl-piperdin-4-yl)naphthalen-1-yl]urea;

1-[5-tert-butyl-2-p-tolyl-2H-pyrazol-3-yl]-3-[4-(6-oxo-1-pyridin-4-yl-1,2,3,6-tetrahydro-pyridin-4-yl)naphthalen-1-yl]urea;

1-[5-tert-butyl-2-(6-methyl-pyridin-3-yl)-2H-pyrazol-3-yl]-3-[4-(6-oxo-1-pyridin-4-yl-1,2,3,6-tetrahydro-pyridin-4-yl)naphthalen-1-yl]urea;

5-tert-butyl-3-{3-[4-(6-oxo-1-pyridin-4-yl-1,2,3,6-tetrahydro-pyridin-4-yl)naphthalen-1-yl]ureido}thiophene-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl amide;

5-tert-butyl-3-{3-[4-(3-morpholin-4-yl-cyclohex-1-enyl)naphthalen-1-yl]ureido}thiophene-2-carboxylic acid methyl ester;

5-tert-butyl-1-methyl-3-{3-[4-(3-morpholin-4-yl-cyclohex-1-enyl)naphthalen-1-yl]ureido}pyrrole-2-carboxylic acid methyl ester; and 5-tert-butyl-1-methyl-3-{3-[4-(3-morpholin-4-yl-cyclohex-1-enyl)naphthalen-1-yl]ureido}pyrrole-2-carboxylic acid methyl amide and the pharmaceutically acceptable derivatives thereof.

In another embodiment of the invention there are provided the following compounds of formula(I) which may be useful in the novel methods described herein:

1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(2-methoxypyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;

1-[3-tert-butyl-1'H-[1,4']bipyrazol-5-yl]-3-[4-(6-(morpholin-4-yl-methyl)pyridin-3-yl)naphthalen-1-yl]-urea;

1-[3-tert-butyl-1'-methyl-1'H-[1,4']bipyrazol-5-yl]-3-[4-(6-(morpholin-4-yl-methyl)pyridin-3-yl)naphthalen-1-yl]-urea;

1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;

1-[3-tert-butyl-1'-methyl-1'H-[1,4']bipyrazol-5-yl]-3-[4-(6-morpholin-4-yl-methyl)phenyl)naphthalen-1-yl]-urea;

1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fur-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin-3-yl)naphthalen-1-yl]urea and the pharmaceutically acceptable derivatives thereof.

In a second broad generic aspect, there is provided a method of treating a cytokine mediated disease or condition chosen from: acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure, said method comprising administering to a patient in need of such treatment a therapeutically effective amount of a compound of the formula (Ia) disclosed in WO 00/55139 which is the PCT case of U.S. application Ser. No. 09/505,582:

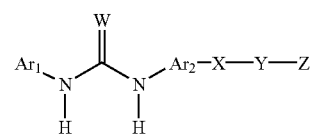

wherein:

Ar$_1$ is:

pyrrole, pyrrolidine, pyrazole, imidazole, oxazole, thiazole, furan and thiophene; wherein Ar$_1$ is optionally substituted by one or more R$_1$, R$_2$ or R$_3$;

Ar$_2$ is:

phenyl, naphthyl, quinoline, isoquinoline, tetrahydronaphthyl, tetrahydroquinoline, tetrahydroisoquinoline, benzimidazole, benzofuran, indanyl, indenyl and indole each being optionally substituted with zero to three R$_2$ groups;

X is:

a C$_{5-8}$ cycloalkyl or cycloalkenyl optionally substituted with one to two oxo groups or one to three C$_{1-4}$ alkyl, C$_{1-4}$ alkoxy or C$_{1-4}$ alkylamino chains each being branched or unbranched;

phenyl, furanyl, thienyl, pyrrolyl, pyrazolyl, imidazolyl, pyridinyl, tetrahydropyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three C$_{1-4}$ alkyl, C$_{1-4}$alkoxy, hydroxy, nitrile, amino, mono- or di-(C$_{1-3}$ alkyl)amino, mono- or di-(C$_{1-3}$ alkylamino)carbonyl, NH$_2$C(O), C$_{1-6}$ alkyl-S(O)$_m$ or halogen;

Y is:

a bond or a C$_{1-4}$ saturated or unsaturated branched or unbranched carbon chain optionally partially or fully halogenated, wherein one or more C atoms are optionally replaced by O, N, or S(O)$_m$ and wherein Y is optionally independently substituted with one to two oxo groups, nitrile, phenyl, hydroxy or one or more C$_{1-4}$ alkyl optionally substituted by one or more halogen atoms;

Z is:

aryl, indanyl, heteroaryl selected from benzimidazolyl, pyridinyl, pyrimidinyl, pyridazinyl, pyrazinyl, imidazolyl, pyrazolyl, triazolyl, tetrazolyl, furanyl, thienyl and pyranyl, heterocycle selected from piperazinyl, tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, C$_{1-6}$ alkyl, C$_{1-6}$ alkoxy, C$_{1-3}$ alkoxy-C$_{1-3}$ alkyl, C$_{1-6}$ alkoxycarbonyl, aroyl, heteroaroyl, heterocycleC$_{1-3}$acyl wherein the heteroaryl and heterocycle are as defined hereinabove in this paragraph, C$_{1-3}$acyl, oxo, hydroxy, pyridinyl-C$_{1-3}$ alkyl, imidazolyl-C$_{1-3}$ alkyl, tetrahydrofuranyl-C$_{1-3}$ alkyl, nitrile-C$_{1-3}$ alkyl, carboxy, phenyl wherein the phenyl ring is optionally substituted with one to two halogen, C$_{1-6}$ alkoxy, hydroxy or mono- or di-(C$_{1-3}$ alkyl) amino, amino-S(O)$_m$, C$_{1-6}$ alkyl-S(O)$_m$ or phenyl-S(O)$_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-S(O)$_m$— or aryl$C_{0-3}$alkyl-S(O)$_m$— each of the aforementioned alkyl and aryl attached to the amino group is optionally substituted with one to two halogen, $C_{1-6}$ alkyl, $C_{1-6}$ alkoxy, hydroxy or mono- or di-($C_{1-3}$ alkyl)amino;

or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-6}$alkyl, amino$C_{1-6}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-S(O)$_m$—, aryl$C_{0-3}$alkyl-S(O)$_m$—, nitrile$C_{1-4}$alkyl or $C_{1-3}$alkoxy$C_{1-3}$alkyl, each of the aforementioned alkyl and aryl attached to the amino group is optionally substituted with one to two halogen, $C_{1-6}$ alkyl, $C_{1-6}$ alkoxy, hydroxy or mono- or di-($C_{1-3}$ alkyl)amino, $C_{1-6}$ alkoxyheteroaryl$C_{0-3}$alkyl, heteroaryl$C_{0-3}$alkyl or heterocycyle$C_{0-3}$alkyl wherein the heteroaryl and heterocycle is hereinabove described in this paragraph, or Z is $C_{1-6}$alkyl branched or unbranched, $C_{1-6}$alkoxy, $C_{1-3}$acylamino, nitrile$C_{1-4}$alkyl, $C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;

$R_1$ is:

a) $C_{1-10}$ branched or unbranched alkyl optionally partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$)alkylaminocarbonyl;

b) $C_{3-7}$ cycloalkyl selected from the group consisting of cyclopropyl, cyclobutyl, cyclopentyl, cyclohexyl, cycloheptyl, bicyclopentyl, bicyclohexyl and bicycloheptyl, each optionally partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;

c) $C_{3-10}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di($C_{1-3}$)alkylaminocarbonyl;

d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) nitrile; or f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:

a $C_{1-6}$ branched or unbranched alkyl optionally partially or fully halogenated and optionally substituted with nitrile, or $R_2$ is acetyl, aroyl, $C_{1-4}$ branched or unbranched alkoxy optionally partially or fully halogenated, halogen, methoxycarbonyl or phenylsulfonyl;

$R_3$ is:

a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of a phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$)alkylamino-S(O)$_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl($R_{13}$)N;

c) cycloalkyl selected from the group consisting of cyclopropyl, cyclobutyl, cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, $C_{1-6}$alkoxycarbonyl$C_{1-6}$alkyl or phenylsulfonyl; or f) $C_{1-6}$ branched or unbranched alkyl optionally partially or fully halogenated;

or $R_1$ and $R_2$ taken together optionally form a fused phenyl or pyridinyl ring;

each $R_8$ and $R_{13}$ is independently selected from the group consisting of:

hydrogen and $C_{1-4}$ branched or unbranched alkyl optionally partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S;

wherein X is directly attached to one or two —Y-Z, and the pharmaceutically acceptable derivatives thereof.

A preferred subgeneric aspect of the invention comprises a method of using the compounds of the formula(Ia) as provided above and wherein:

$Ar_2$ is naphthyl, tetrahydronaphthyl, indanyl or indenyl and W is O.

A more preferred subgeneric aspect of the invention comprises a method of using the compounds of the formula (Ia) as provided above and wherein:

$Ar_1$ is thiophene or pyrazole each substituted independently by one to three $R_1$, $R_2$ or $R_3$;

X is:

a $C_{5-7}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;

phenyl, indanyl, furanyl, thienyl, imidazolyl, pyridinyl, pyrazinyl, tetrahydrapyridinyl, pyrimidinyl, pyridinonyl, piperdinyl, benzimidazole or piperazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-S(O)$_m$ or halogen;

Y is:

a bond or a $C_{1-4}$ saturated or unsaturated branched or unbranched carbon chain optionally partially or fully halogenated, wherein one or more C atoms are optionally replaced by O or N, and wherein Y is optionally independently substituted with one to two oxo groups, nitrile, phenyl, hydroxy or one or more $C_{1-4}$ alkyl optionally substituted by one or more halogen atoms;

Z is:

phenyl, heteroaryl selected from pyridinyl, imidazolyl, furanyl and thienyl, heterocycle selected from piperazinyl, 2-oxa-5-aza-bicyclo[2.2.1]heptanyl, pentamethylene sulfidyl, pentamethylene sulfoxidyl, pentamethylene sulfonyl, tetrahydrofuranyl, morpholino, thiomorpholino and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-S(O)$_m$, $C_{1-6}$ alkyl-S(O)$_m$ or phenyl-S(O)$_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-S(O)$_m$— or aryl$C_{0-3}$alkyl-S(O)$_m$— each of the aforementioned alkyl and aryl attached to the amino group are optionally substituted with one to two halogen, $C_{1-6}$ alkyl or $C_{1-6}$ alkoxy;

or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by aroyl, $C_{1-3}$acyl, $C_{1-6}$alkyl, $C_{1-5}$ alkoxy$C_{1-3}$ alkyl, pyridinyl$C_{1-3}$alkyl, tetrahydrafuranyl$C_{1-3}$alkyl, nitrile$C_{1-4}$alkyl or phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated;

cyclopropyl, cyclobutyl, cyclopentyl, cyclohexyl and cycloheptyl optionally partially or fully halogenated and optionally substituted with one to three $C_{1-3}$ alkyl groups, or an analog of such cycloalkyl group wherein one to three ring methylene groups are replaced by groups independently selected from the group consisting of O, S and NH;

$C_{3-10}$ branched alkenyl optionally partially or fully halogenated and optionally substituted with one to three $C_{1-5}$ branched or unbranched alkyl;

cyclopentenyl and cyclohexenyl optionally substituted with one to three $C_{1-3}$ alkyl groups;

$R_2$ is:

a $C_{1-6}$ branched or unbranched alkyl optionally partially or fully halogenated and optionally substituted with nitrile;

$R_3$ is:

phenyl or heterocyclic group selected from the group consisting of pyridinyl, pyrimidinyl, pyrazinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally be partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, heteraryloxy wherein the heterocyclic moiety is selected from the group hereinabove described in this paragraph, nitro, amino, mono- or di-$(C_{1-3})$alkylamino, phenylamino, naphthylamino, heterocyclylamino wherein the heterocyclyl moiety is selected from the group hereinabove described in this paragraph, $NH_2C(O)$, a mono- or di-$(C_{1-3})$alkyl aminocarbonyl, $C_{1-5}$ alkyl-$C(O)$—$C_{1-4}$ alkyl, amino-$C_{1-5}$ alkyl, mono- or di-$(C_{1-3})$alkylamino-$C_{1-5}$ alkyl, amino-$S(O)_2$, di-$(C_{1-3})$alkylamino-$S(O)_2$, $R_4$—$C_{1-5}$ alkyl, $R_5$—$C_{1-5}$alkoxy, $R_6$—$C(O)$—$C_{1-5}$ alkyl and $R_7$—$C_{1-5}$alkyl($R_8$)N, carboxy-mono- or di-$(C_{1-5})$-alkyl-amino;

a fused aryl selected from the group consisting of benzocyclobutanyl, indanyl, indenyl; wherein the fused aryl is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-$(C_{1-3})$alkylamino, phenylamino, naphthylamino, heterocyclylamino wherein the heterocyclyl moiety is selected from the group hereinabove described in this paragraph, $NH_2C(O)$, a mono- or di-$(C_{1-3})$alkyl aminocarbonyl, $C_{1-4}$ alkyl-$OC(O)$, $C_{1-5}$ alkyl-$C(O)$—$C_{1-4}$ branched or unbranched alkyl, an amino-$C_{1-5}$ alkyl, mono- or di-$(C_{1-3})$alkylamino-$C_{1-5}$ alkyl, $R_9$—$C_{1-5}$ alkyl, $R_{10}$—$C_{1-5}$ alkoxy, $R_{11}$—$C(O)$—$C_{1-5}$ alkyl and $R_{12}$—$C_{1-5}$ alkyl($R_{13}$)N;

cycloalkyl selected from the group consisting of cyclopropyl, cyclobutyl, cyclopentyl, cyclohexyl, cycloheptyl, wherein the cycloalkyl is optionally partially or fully halogenated and optionally substituted with one to three $C_{1-3}$ alkyl groups;

$C_{1-6}$alkoxycarbonyl$C_{1-6}$alkyl;

or $R_1$ and $R_2$ taken together optionally form a fused phenyl or pyridinyl ring;

each $R_8$ and $R_{13}$ is independently selected from the group consisting of: hydrogen and $C_{1-4}$ branched or unbranched alkyl optionally partially or fully halogenated; and each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

wherein X is directly attached to one —Y-Z.

A yet more preferred subgeneric aspect of the invention comprises a method of using the compounds of the formula (Ia), as described in the immediate previous paragraph, wherein:

$Ar_1$ is pyrazole;

X is:

cyclopentenyl, cyclohexenyl, cycloheptenyl, optionally substituted with an oxo group or one to three $C_{1-4}$ alkyl, $C_{1-4}$ alkoxy or $C_{1-4}$ alkylamino chains each being branched or unbranched;

phenyl, furanyl, thienyl, pyridinyl, pyrazinyl piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-aza-bicyclo[2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrite, carboxy, phenyl wherein the phenyl ring is optionally substituted with one to two halogen, $C_{1-6}$ alkoxy, hydroxy or mono- or di-$(C_{1-3}$ alkyl)amino, amino-$S(O)_m$, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-$(C_{1-3}$ alkyl)amino;

or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$—, pyridinyl$C_{0-3}$alkyl, tetrahydrafuranyl$C_{0-3}$alkyl, or aryl$C_{0-3}$ alkyl-$S(O)_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{0-3}$alkyl, halogen, nitrile, amino wherein the N atom is optionally independently mono- or di-substituted by $C_{1-6}$alkyl, pyridinyl$C_{0-3}$alkyl, tetrahydrafuranyl$C_{0-3}$alkyl, $C_{1-5}$ alkoxy$C_{1-3}$ alkyl, $C_{1-3}$acyl, nitrile$C_{1-4}$alkyl or phenyl wherein the phenyl ring is optionally substituted with one to two halogen, $C_{1-6}$ alkoxy, hydroxy or mono- or di-$(C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated;

cyclopropyl, cyclobutyl, cyclopentanyl, cyclohexanyl and cycloheptanyl optionally partially or fully halogenated and optionally substituted with one to three $C_{1-3}$ alkyl groups, or an analog of such cycloalkyl group wherein one to three ring methylene groups are replaced by groups independently selected from the group consisting of O, S and NH;

$C_{3-10}$ branched alkenyl optionally partially or fully halogenated and optionally substituted with one to three $C_{1-3}$ branched or unbranched alkyl;

cyclopentenyl and cyclohexenyl optionally substituted with one to three $C_{1-3}$ alkyl groups;

$R_2$ is:

a $C_{1-6}$ branched or unbranched alkyl optionally partially or fully halogenated and optionally substituted with nitrile;

$R_3$ is:

phenyl or heterocyclic group selected from the group consisting of pyridinyl, pyrimidinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, phenyl $C_{1-5}$ alkyl, halogen, hydroxy, oxo, nitrile, $C_{1-3}$ alkoxy optionally partially or fully halogenated, $C_{1-3}$thioalkyl, $C_{1-3}$thioalkyl$C_{1-5}$alkyl, amino, mono- or di-($C_{1-3}$)alkylamino, $NH_2C(O)$ or a mono- or di-($C_{1-3}$)alkyl aminocarbonyl, $C_{1-6}$alkoxycarbonyl$C_{1-6}$alkyl;

or $R_3$ is cyclopropyl or cyclopentyl each optionally partially or fully halogenated and optionally substituted with one to three $C_{1-3}$ alkyl groups or $R_1$ and $R_2$ taken together optionally form a fused phenyl or pyridinyl ring.

A yet further preferred subgeneric aspect of the invention comprises a method of using the compounds of the formula (Ia), as described in the immediate previous paragraph, and wherein:

Y is —$CH_2$—, —O—$(CH_2)_{0-3}$—, —$CH_2CH_2$—, —$CH_2NH$—, —$CH_2CH_2$—$NH$—, $NH$—$CH_2CH_2$—, —$CH_2$—$NH$—$CH_2$—, —$NH$—, —$NH$—$C(O)$—, —$C(O)$—, —$CH(OH)$—, —$CH_2(CH_2CH_3)$— or a bond;

X is:

cyclohexenyl optionally substituted with an oxo group or one to three $C_{1-4}$ alkyl, $C_{1-4}$ alkoxy or $C_{1-4}$ alkylamino chains each being branched or unbranched; phenyl, pyridinyl, pyrazinyl, piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-aza-bicyclo[2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino or aminocarbonyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-3}$alkyl, pyridinyl$C_{1-2}$alkyl, tetrahydrafuranyl$C_{1-2}$alkyl, $C_{1-3}$ alkoxy$C_{1-3}$ alkyl, $C_{1-3}$acyl, nitrile$C_{1-4}$alkyl, phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated;

$R_2$ is:

a $C_{1-3}$ branched or unbranched alkyl optionally partially or fully halogenated and optionally substituted with nitrile;

$R_3$ is:

phenyl or heterocyclic group selected from the group consisting of pyridinyl, pyrimidinyl, and pyrazolyl, wherein such phenyl or heterocyclic group is optionally substituted with one to five groups selected from the group consisting of $C_{1-3}$ branched or unbranched alkyl which is optionally partially or fully halogenated, $C_{1-3}$ alkoxy which optionally partially or fully halogenated, $C_{1-3}$thioalkyl, $C_{1-3}$thioalkyl$C_{1-5}$alkyl, amino or $NH_2C(O)$;

$C_{1-3}$alkoxycarbonyl;

or $R_3$ is cyclopropyl or cyclopentyl each optionally partially or fully halogenated and optionally substituted with one to three $C_{1-3}$ alkyl groups.

A further preferred subgeneric aspect of the invention comprises a method of using the compounds of the formula (Ia), as described in the immediate previous paragraph, and wherein:

$Ar_1$ is 5-tert-butyl-pyrazol-3-yl; wherein the pyrazole ring is substituted independently by one to two $R_2$ or $R_3$;

X is:

cyclohexenyl;

phenyl, pyridinyl, pyrazinyl, piperidinyl or pyrimidinyl each being optionally independently substituted with $C_{1-2}$alkoxy or hydroxy;

Z is:

phenyl, heteroaryl selected from pyridinyl and furanyl, heterocycle selected from 2-oxa-5-aza-bicyclo[2.2.1]heptanyl, pentamethylene sulfidyl, pentamethylene sulfoxidyl, tetrahydrofuranyl, piperazinyl, morpholino, thiomorpholino and piperidinyl, each of the aforementioned Z are optionally substituted with one to three $C_{1-3}$ alkyl, $C_{1-3}$ alkoxy, oxo , hydroxy or $NH_2C(O)$—;

or Z is hydroxy$C_{1-3}$alkyl, amino wherein the N atom is optionally independently mono- or di-substituted by pyridinylmethyl, tetrahydrafuranylmethyl, $C_{1-3}$ alkoxy$C_{1-3}$ alkyl, $C_{1-3}$acyl or nitrile$C_{1-4}$alkyl, or Z is nitrile$C_{1-4}$alkyl;

$R_3$ is:

phenyl or heterocyclic group selected from the group consisting of pyridinyl, pyrimidinyl, and pyrazolyl, wherein such phenyl or heterocyclic group is optionally substituted with one to two groups selected from the group consisting of $C_{1-2}$ alkyl which is optionally partially or fully halogenated, $C_{1-2}$ alkoxy which optionally partially or fully halogenated, $C_{1-2}$thioalkyl, $C_{1-2}$thioalkyl$C_{1-3}$ alkyl, amino or $NH_2C(O)$;

$C_{1-3}$alkoxycarbonyl;

or $R_3$ is cyclopropyl or cyclopentyl each optionally partially or fully halogenated and optionally substituted with one to three $C_{1-3}$ alkyl groups.

A still yet further preferred subgeneric aspect of the invention comprises a method of using the compounds of the formula (Ia), as described in the immediate previous paragraph, and wherein X is pyridinyl.

A still yet further preferred subgeneric aspect of the invention comprises a method of using the compounds of the formula (Ia), as described in the immediate previous paragraph, and wherein:

the pyridinyl is attached to $Ar_1$ via the 3-pyridinyl position.

The following compounds are representative of the compounds of formula(Ia) which are useful in the novel methods described herein:

1-[5-tert-butyl-2-p-tolyl-2H-pyrazol-3-yl]-3-[4-(4-morpholin-4-yl-methylphenyl)-naphthalen-1-yl]-urea;
1-[5-tert-butyl-2-p-tolyl-2H-pyrazol-3-yl]-3-[3-(4-morpholin-4-yl-methylphenyl)-naphthalen-1-yl]-urea;
1-[5-tert-butyl-2-p-tolyl-2H-pyrazol-3-yl]-3-[4-(5-morpholin-4-yl-methylfuran-2-yl)-naphthalen-1-yl]-urea;
1-[5-tert-butyl-2-p-tolyl-2H-pyrazol-3-yl]-3-[4-(3-(morpholin-4-yl-methyl)cyclohexenyl)-naphthalen-1-yl]-urea;
1-[5-tert-butyl-2-p-tolyl-2H-pyrazol-3-yl]-3-[4-(2-(4-morpholin-4-yl)ethylphenyl)-naphthalen-1-yl]-urea;
1-[5-tert-butyl-2-p-tolyl-2H-pyrazol-3-yl]-3-[4-(4-dimethylaminomethylphenyl)-naphthalen-1-yl]-urea;
1-[5-tert-butyl-2-p-tolyl-2H-pyrazol-3-yl]-3-[4-(5-(morpholin-4-yl-methyl)pyridin-2-yl)-naphthalen-1-yl]-urea;
1-[5-tert-butyl-2-p-tolyl-2H-pyrazol-3-yl]-3-[4-(6-(morpholin-4-yl-methyl)pyridin-3-yl)-naphthalen-1-yl]-urea;
1-[5-tert-butyl-2-(6-methyl-pyridin-3-yl)-2H-pyrazol-3-yl]-3-[4-(6-(morpholin-4-yl-methyl)pyridin-3-yl)-naphthalen-1-yl]-urea;
1-[5-tert-butyl-2-methyl-2H-pyrazol-3-yl]-3-[4-(6-(morpholin-4-yl-methyl)pyridin-3-yl)-naphthalen-1-yl]-urea;
1-[5-tert-butyl-2-(6-methyl-pyridin-3-yl)-2H-pyrazol-3-yl]-3-[4-(3-(2-(morpholin-4-yl)ethylamino)cyclohexenyl)-naphthalen-1-yl]-urea;
1-[5-tert-butyl-2-p-tolyl-2H-pyrazol-3-yl]-3-[4-(3,4-(morpholin-4-yl-methyl)phenyl)-naphthalen-1-yl]-urea;
1-[5-tert-butyl-2-p-tolyl-2H-pyrazol-3-yl]-3-[4-(4-methylpiperzin-1-yl-methyl)phenyl)-naphthalen-1-yl]-urea;
1-[5-tert-butyl-2-p-tolyl-2H-pyrazol-3-yl]-3-[4-(piperdin-1-yl-methyl)phenyl)-naphthalen-1-yl]-urea;
1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;
1-[5-tert-butyl-2-p-tolyl-2H-pyrazol-3-yl]-3-[4-(4-(2-(pyridin-4-yl)ethylaminomethyl)phenyl)naphthalen-1-yl]-urea;
1-[5-tert-butyl-2-p-tolyl-2H-pyrazol-3-yl]-3-[4-(4-(pyridin-3-yl-methylaminomethyl)phenyl)naphthalen-1-yl]-urea;
1-[5-tert-butyl-2-(6-methyl-pyridin-3-yl)-2H-pyrazol-3-yl]-3-[4-(4-(3,4-dimethoxyphenylmethyl)-3-hydroxyphenyl)naphthalen-1-yl]-urea;
1-[5-tert-butyl-2-p-tolyl-2H-pyrazol-3-yl]-3-[4-(6-oxo-1,6-dihydro-pyridin-3-yl)naphthalen-1-yl]-urea;
1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;
1-[5-tert-butyl-2-(6-methyl-pyridin-3-yl)-2H-pyrazol-3-yl]-3-[4-(4-(morpholin-4-yl-methyl)imidazol-1-yl)naphthalen-1-yl]-urea;
1-[5-tert-butyl-2-p-tolyl-2H-pyrazol-3-yl]-3-[4-(4-(morpholin-4-yl-methyl)imidazol-1-yl)naphthalen-1-yl]-urea;
1-[5-tert-butyl-2-(6-methyl-pyridin-3-yl)-2H-pyrazol-3-yl]-3-[4-(4-(furan-3-yl-methyl)-3-hydroxyphenyl)naphthalen-1-yl]-urea;
1-[5-tert-butyl-2-(6-methyl-pyridin-3-yl)-2H-pyrazol-3-yl]-3-[4-(6-(4-hydroxybutylamino)pyridin-3-yl)-naphthalen-1-yl]-urea;
1-[5-tert-butyl-2-(6-methyl-pyridin-3-yl)-2H-pyrazol-3-yl]-3-[4-(4-(pyridin-3-yl-methyl)-3-hydroxyphenyl)naphthalen-1-yl]-urea;
1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(4-(imidazol-2-yl-methyl)-3-hydroxyphenyl)naphthalen-1-yl]-urea;
1-[5-tert-butyl-2-(6-methyl-pyridin-3-yl)-2H-pyrazol-3-yl]-3-[4-(4-(3-hydroxymorpholin-4-yl-methyl)phenyl)naphthalen-1-yl]-urea;
1-[5-tert-butyl-2-(6-methyl-pyridin-3-yl)-2H-pyrazol-3-yl]-3-[4-(4-(N-2methoxyethy-N-methylaminomethyl)phenyl)naphthalen-1-yl]-urea;
1-[5-tert-butyl-2-(6-methyl-pyridin-3-yl)-2H-pyrazol-3-yl]-3-[4-(4-(4-hydroxymorpholin-(4-yl-methyl)phenyl)naphthalen-1-yl]-urea;
1-[5-tert-butyl-2-(6-methyl-pyridin-3-yl)-2H-pyrazol-3-yl]-3-[4-(3-(morpholin-4-yl-methyl)cyclohexenyl)-naphthalen-1-yl]-urea;
1-[5-tert-butyl-2-(6-methyl-pyridin-3-yl)-2H-pyrazol-3-yl]-3-[4-(4-(tetrahydrofuran-3-yl-methyl)-3-hydroxyphenyl)naphthalen-1-yl]-urea;
1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;
1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;
1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;
1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;
1-[5-tert-butyl-2-p-tolyl-2H-pyrazol-3-yl]-3-[4-(1-morpholin-4-yl-indan-5-yl)-naphthalen-1-yl]-urea;
1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]urea;
1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;
1-[5-tert-butyl-2-(6-methyl-pyridin-3-yl)-2H-pyrazol-3-yl]-3-[4-(4-(3-carboxamidomorpholin-4-yl-methyl)phenyl)naphthalen-1-yl]urea;
1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;
1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;
1-[3-tert-butyl-1'H-[1,4']bipyrazol-5-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(4-(furan-2-yl-methyl)-3-methoxyphenyl)naphthalen-1-yl]-urea;
1-[5-tert-butyl-2-(6-methyl-pyridin-3-yl)-2H-pyrazol-3-yl]-3-[4-(5-(morpholin-4carbonyl)pyrazin-2-yl)naphthalen-1-yl]-urea;

1-[5-tert-butyl-2-(6-methyl-pyridin-3-yl)-2H-pyrazol-3-yl]-3-[4-(6-(tetrahydrothiopyran-4-yl-amino)pyridin-3-yl)-naphthalen-1-yl]-urea;

1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;

1-[5-tert-butyl-2-(2-methoxypyridirin-5-yl)-2H-pyrazol-3-yl]-3-[4-(6-(morpholin-4-yl-methyl)pyridin-3-yl)-naphthalen-1-yl]-urea;

1-[5-tert-butyl-2-(2-aminopyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-oxo-1,6-dihydropyridin-3-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;

1-[5-tert-butyl-2-(6-methyl-pyridin-3-yl)-2H-pyrazol-3-yl]-3-[4-(6-(2-oxa-5-aza-bicyclo[2.2.1]hept-5-yl-methyl)pyridin-3-yl)-naphthalen-1-yl]-urea;

1-[5-tert-butyl-2-p-tolyl-2H-pyrazol-3-yl]-3-[4-(4-(3-carbamylphenyl)naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;

1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)amino)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)-N-methylamino)pyridin-3-yl)-naphthalen-1-yl]-urea;

1-[3-tert-butyl-1'-methyl-1'H-[1,4']bipyrazol-5-yl]-3-[4-(6-(morpholin-4-yl-methyl)pyridin-3-yl)naphthalen-1-yl]-urea;

1-[5-tert-butyl-2-benzyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(4-(N-N-di-(2-cyanoethyl)aminomethyl)phenyl)-naphthalen-1-yl]-urea;

1-[5-tert-butyl-2-p-tolyl-2H-pyrazol-3-yl]-3-[4-(4-(4-carbamylphenyl)naphthalen-1-yl]-urea;

1-[5-tert-butyl-2-(6-methyl-pyridin-3-yl)-2H-pyrazol-3-yl]-3-[4-(6-(1-oxo-tetrahydrothiopyran-4-yl-amino)pyridin-3-yl)-naphthalen-1-yl]-urea;

1-[5-tert-butyl-2-(6-methyl-pyridin-3-yl)-2H-pyrazol-3-yl]-3-[4-(6-(tetrahydropyran-4yl-amino)pyridin-3-yl)-naphthalen-1-yl]-urea;

1-[3-tert-butyl-1'-(3-cyanopropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(3-methanesulfinylphenyl)naphthalen-1-yl]-urea;

1-[5-tert-butyl-2-p-tolyl-2H-pyrazol-3-yl]-3-[4-(3-methanesulfonylphenyl)naphthalen-1-yl]-urea;

1-[5-tert-butyl-2-p-tolyl-2H-pyrazol-3-yl]-3-[4-(3-sulfonamidophenyl)naphthalen-1-yl]-urea;

1-[5-tert-butyl-2-p-tolyl-2H-pyrazol-3-yl]-3-[4-(3-(morpholin-4-yl)carbonylphenyl)naphthalen-1-yl]-urea;

1-[5-tert-butyl-2-(6-methyl-pyridin-3-yl)-2H-pyrazol-3-yl]-3-[4-(5-(tetrahydrothiopyran-4yl-amino)pyrazin-2-yl)-naphthalen-1-yl]-urea;

1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;

1-[5-tert-butyl-2-p-tolyl-2H-pyrazol-3-yl]-3-[4-(6-(morpholin-4-yl-4-carbonyl)phenyl)-naphthalen-1-yl]-urea;

1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(5-(morpholin-4-yl-carbonyl)pyridin-3-yl)-naphthalen-1-yl]-urea;

1-[5-tert-butyl-2-(6-methyl-pyridin-3-yl)-2H-pyrazol-3-yl]-3-[4-(5-(morpholin-4-yl-methyl)pyrazin-2-yl)-naphthalen-1-yl]-urea;

1-[5-tert-butyl-2-(6-methyl-pyridin-3-yl)-2H-pyrazol-3-yl]-3-[4-(6-aminopyridin-3-yl)naphthalen-1-yl]-urea;

1-[5-tert-butyl-2-(6-methyl-pyridin-3-yl)-2H-pyrazol-3-yl]-3-[4-(6-(1-methylpiperidin-4-yl-amino)pyridin-3-yl)naphthalen-1-yl]-urea;

1-[5-tert-butyl-2-(2-methylpyrimidin-5-yl)-2H-pyrazol-3-yl]-3-[4-(6-(2-methyl-3-oxo-piperzin-1-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(morpholin-4-yl-carbonyl)pyridin-3-yl)naphthalen-1-yl]-urea;

1-[5-tert-butyl-2-(2-methylpyrimidin-5-yl)-2H-pyrazol-3-yl]-3-[4-(6-(N,N-di-(2-methoxyethyl)aminomethyl)pyridin-3-yl)naphthalen-1-yl]-urea;

1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(tetrahydropyran-4-yl-amino)pyridin-3-yl)naphthalen-1-yl]-urea;

1-[5-tert-butyl-2-(2-methylpyrimidin-5-yl)-2H-pyrazol-3-yl]-3-[4-(5-(morpholin-4-yl-methyl)pyrazin-2-yl)naphthalen-1-yl]-urea;

1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(6-(2-methyl-3-oxo-piperz-1-yl-methyl)pyridin-3-yl)naphthalen-1-yl]-urea;

1-[5-tert-butyl-2-p-tolyl-2H-pyrazol-3-yl]-3-[4-(6-(pyridin-3-yl-oxy)pyridin-3-yl)naphthalen-1-yl]urea 1-[5-tert-butyl-2-p-tolyl-2H-pyrazol-3-yl]-3-[4-(6-(pyridin-3-yl-amino)pyridin-3-yl)naphthalen-1-yl]-urea;

1-[5-tert-butyl-2-(2-methoxypyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(5-carbamylpyridin-3-yl)naphthalen-1-yl]-urea;

1-[5-tert-butyl-2-(2-aminopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(4-(morpholin-4-yl-methyl)phenyl)naphthalen-1-yl]-urea;

1-[3-tert-butyl-1'-methyl-1'H-[1,4']bipyrazol-5-yl]-3-[4-(6-(morpholin-4-yl-methyl)phenyl)naphthalen-1-yl]-urea;

1-[5-tert-butyl-2-(2-cyclopropylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(2-(pyridin-3-yl-amino)pyrimidin-5-yl)naphthalen-1-yl]-urea;

1-[5-tert-butyl-2-p-tolyl-2H-pyrazol-3-yl]-3-[4-(6-(1-oxo-tetrahydrothiopyran-4-yl-amino)pyridin-3-yl)naphthalen-1-yl]-urea;

1-[5-tert-butyl-2-p-tolyl-2H-pyrazol-3-yl]-3-[4-(6-(thiomorpholin-4-yl-methyl)pyridin-3-yl)naphthalen-1-yl]-urea;

1-[5-tert-butyl-2-p-tolyl-2H-pyrazol-3-yl]-3-[4-(3-benzyl-3H-imidazo[4,5-b]pyridin-6-yl)naphthalen-1-yl]-urea;

1-[5-tert-butyl-2-(6-methyl-pyridin-3-yl)-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(2-(morpholin-4-yl-carbonyl)pyrimidin-5-yl)naphthalen-1-yl]-urea;

1-[5-tert-butyl-2-p-tolyl-2H-pyrazol-3-yl]-3-[4-(2-(morpholin-4-yl-methyl)pyrimidin-5-yl)naphthalen-1-yl]-urea;

1-[5-tert-butyl-2-p-tolyl-2H-pyrazol-3-yl]-3-[4-(3-amino-4-carbamylphenyl)naphthalen-1-yl]-urea;

1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;

1-[5-tert-butyl-2-p-tolyl-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(6-(hydroxy-pyridin-3-yl-methyl)pyridin-3-yl)naphthalen-1-yl]-urea;

1-[5-tert-butyl-2-(2-methylpyrimidin-5-yl)-2H-pyrazol-3-yl]-3-[4-(2-(morpholin-4-yl-methyl)pyrimidin-5-yl)naphthalen-1-yl]-urea;

and the pharmaceutically acceptable derivatives thereof.

In another embodiment of the invention there are provided the following compounds of formula(Ia) which are useful in the novel methods described herein:

1-[5-tert-butyl-2-p-tolyl-2H-pyrazol-3-yl]-3-[4-(5-(morpholin-4-yl-methyl)pyridin-2-yl)-naphthalen-1-yl]-urea;

1-[5-tert-butyl-2-p-tolyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;

1-[5-tert-butyl-2-p-tolyl-2H-pyrazol-3-yl]-3-[4-(4-(pyridin-3-yl-methylaminomethyl)phenyl)naphthalen-1-yl]-urea;

1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;

1-[5-tert-butyl-2-(6-methyl-pyridin-3-yl)-2H-pyrazol-3-yl]-3-[4-(6-(4-hydroxybutylamino)pyridin-3-yl)-naphthalen-1-yl]-urea;

1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(3-hydroxypiperidin-1-yl-methyl)phenyl)naphthalen-1-yl]-urea;

1-[5-tert-butyl-2-(6-methyl-pyridin-3-yl)-2H-pyrazol-3-yl]-3-[4-(4-(4-hydroxymorpholin-4-yl-methyl)phenyl)naphthalen-1-yl]-urea;

1-[5-tert-butyl-2-(6-methyl-pyridin-3-yl)-2H-pyrazol-3-yl]-3-[4-(3-(morpholin-4-yl-methyl)cyclohexenyl)-naphthalen-1-yl]-urea;

1-[5-tert-butyl-2-(6-methyl-pyridin-3-yl)-2H-pyrazol-3-yl]-3-[4-(4-(tetrahydrofuran-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;

1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;

1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;

1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;

1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(3-carboxamidopiperidin-1-yl-methyl)phenyl)naphthalen-1-yl]-urea;

1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;

1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;

1-[3-tert-butyl-1'H-[1,4']bipyrazol-5-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(tetrahydrothiopyran-4-yl-amino)pyridin-3-yl)-naphthalen-1-yl]-urea;

1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;

1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(2-aminoypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;

1-[5-tert-butyl-2-(6-methyl-pyridin-3-yl)-2H-pyrazol-3-yl]-3-[4-(6-(2-oxa-5-aza-bicyclo[2.2.1]hept-5-yl-methyl)pyridin-3-yl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;
1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;
1-[3-tert-butyl-1'-methyl-1'H-[1,4']bipyrazol-5-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(6-(1-oxo-tetrahydrothiopyran-4-yl-amino)pyridin-3-yl)-naphthalen-1-yl]-urea;
1-[5-tert-butyl-2-(6-methyl-pyridin-3-yl)-2H-pyrazol-3-yl]-3-[4-(6-(tetrahydropyran-4yl-amino)pyridin-3-yl)-naphthalen-1-yl]-urea;
1-[5-tert-butyl-2-(6-methyl-pyridin-3-yl)-2H-pyrazol-3-yl]-3-[4-(5-(tetrahydrothiopyran-4yl-amino)pyrazin-2-yl)-naphthalen-1-yl]-urea;
1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;
1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;
1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;
1-[5-tert-butyl-2-(2-methylpyrimidin-5-yl)-2H-pyrazol-3-yl]-3-[4-(6-(tetrahydropyran-4-yl-amino)pyridin-3-yl)naphthalen-1-yl]-urea;
1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;
1-[5-tert-butyl-2-(2-aminopyrimidin-5-yl)-2H-pyrazol-3-yl]-3-[4-(6-(morpholin-4-yl-methyl)pyridin-3-yl)naphthalen-1-yl]-urea;
1-[3-tert-butyl-1'-methyl-1'H-[1,4']bipyrazol-5-yl]-3-[4-(6-(morpholin-4-yl-methyl)phenyl)naphthalen-1-yl]-urea;
1-[5-tert-butyl-2-p-tolyl-2H-pyrazol-3-yl]-3-[4-(6-(1-oxo-tetrahydrothiopyran-4-yl-amino)pyridin-3-yl)naphthalen-1-yl]-urea;
1-[5-tert-butyl-2-p-tolyl-2H-pyrazol-3-yl]-3-[4-(6-(thiomorpholin-4-yl-methyl)pyridin-3-yl)naphthalen-1-yl]-urea;
1-[5-tert-butyl-2-p-tolyl-2H-pyrazol-3-yl]-3-[4-(2-(morpholin-4-yl-carbonyl)pyrimidin-5-yl)naphthalen-1-yl]-urea;
1-[5-tert-butyl-2-p-tolyl-2H-pyrazol-3-yl]-3-[4-(2-(morpholin-4-yl-methyl)pyrimidin-5-yl)naphthalen-1-yl]-urea;
1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;
1-[5-tert-butyl-2-(2-methylpyrimidin-5-yl)-2H-pyrazol-3-yl]-3-[4-(2-(morpholin-4-yl-methyl)pyrimidin-5-yl)naphthalen-1-yl]-urea and the pharmaceutically acceptable derivatives thereof.

In a third broad generic aspect, there is provided a method of treating a cytokine mediated disease or condition chosen from: acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure, said method comprising administering to a patient in need of such treatment a therapeutically effective amount of a compound of the formula (II) disclosed in WO 00/55139 which is the PCT case of U.S. application Ser. No. 09/505,582:

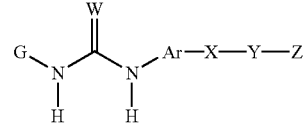

wherein:
G is:
an aromatic $C_{6-10}$ carbocycle or a nonaromatic $C_{3-10}$ carbocycle saturated or unsaturated;
a 6–10 membered heteroaryl containing 1 or more heteroatoms chosen from O, N and S;
a 5–8 membered monocyclic heterocycle containing one or more heteroatoms chosen from O, N and S;
or
an 8–11 membered bicyclic heterocycle, containing one or more heteroatoms chosen from O, N and S;

wherein G is substituted by one or more $R_1$, $R_2$ or $R_3$;
Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;
X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains;
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl;
Y is:
a bond or a $C_{1-4}$ saturated or unsaturated branched or unbranched carbon chain optionally partially or fully halogenated, wherein one or more methylene groups are optionally replaced by O, N, or $S(O)_m$ and wherein Y is optionally independently substituted with one to two oxo groups, phenyl or one or more $C_{1-4}$ alkyl optionally substituted by one or more halogen atoms;
Z is:
phenyl, pyridinyl, pyrimidinyl, pyridazinyl, pyrazinyl, imidazolyl, pyrazolyl, triazolyl, tetrazolyl, furanyl, thienyl, pyranyl each being optionally substituted with one to three halogen, $C_{1-6}$ alkyl, $C_{1-6}$ alkoxy, hydroxy, amino, mono- or di-($C_{1-3}$ alkyl)amino, $C_{1-6}$ alkyl-$S(O)_m$, CN, $CONH_2$, COOH or phenylamino wherein the phenyl ring is optionally substituted with one to two halogen, $C_{1-6}$ alkyl or $C_{1-6}$ alkoxy;
tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, thiomorpholino sulfonyl, piperidinyl, piperidinonyl, piperazinyl, tetrahydropyrimidonyl, cyclohexanonyl, cyclohexanolyl, pentamethylene sulfidyl, pentamethylene sulfoxidyl, pentamethylene sulfonyl, tetramethylene sulfide, tetramethylene sulfoxidyl or tetramethylene sulfonyl each being optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, $CONH_2$, phenylamino-$C_{1-3}$ alkyl or $C_{1-3}$ alkoxy-$C_{1-3}$ alkyl;

halogen, $C_{1-4}$ alkyl, nitrile, amino, hydroxy, $C_{1-6}$ alkoxy, $NH_2C(O)$, mono- or di($C_{1-3}$alkyl) aminocarbonyl, mono- or di($C_{1-6}$alkyl)amino, secondary or tertiary amine wherein the amino nitrogen is covalently bonded to $C_{1-3}$ alkyl or $C_{1-5}$alkoxyalkyl, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, carboxamide-$C_{1-3}$ alkyl, phenyl, wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$, wherein the phenyl ring is optionally substituted with one to two halogen, $C_{1-6}$ alkoxy, hydroxy, halogen or mono- or di-($C_{1-3}$ alkyl) amino;

$C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:

$C_{1-10}$ alkyl optionally be partially or fully halogenated, and optionally substituted with one to three $C_{3-10}$ cycloalkanyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl)amino, and mono- or di($C_{1-3}$alkyl) aminocarbonyl;

cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;

phenyloxy or benzyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloaryl group wherein one to two ring methyne groups are independently replaced by N;

cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;

$C_{3-10}$ branched or unbranced alkenyl each being optionally partially or fully halogenated, and optionally be substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with zero to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di($C_{1-3}$alkyl)aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

nitrile, halogen;

methoxycarbonyl, ethoxycarbonyl and propoxycarbonyl;

silyl containing three $C_{1-4}$ alkyl groups optionally partially or fully halogenated;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, pyrrolidinyl, pyrrolyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is a $C_{1-6}$ branched or unbranched alkyl optionally partially or fully halogenated, acetyl, aroyl, $C_{1-4}$ branched or unbranched alkoxy, each being optionally partially or fully halogenated, halogen, nitrile, methoxycarbonyl, $C_{1-3}$ alkyl-$S(O)_m$ optionally partially or fully halogenated, or phenylsulfonyl;

$C_{1-6}$ alkoxy, hydroxy, amino, or mono- or di-($C_{1-4}$ alkyl) amino, nitrile, halogen;

$OR_6$;

nitro; or mono- or di-($C_{1-4}$ alkyl)amino-$S(O)_2$ optionally partially or fully halogenated, or $H_2NSO_2$;

each $R_3$ is independently:

phenyl, naphthyl, morpholinyl, pyridinyl, pyrimidinyl, pyrazinyl, pyridazinyl, pyrrolyl, pyrrolidinyl, imidazolyl, pyrazolyl, thiazolyl, oxazoyl, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkyloxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alkyl)amino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-$C(O)$—$C_{1-4}$ alkyl, amino-$C_{1-5}$ alkyl, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{1-5}$ alkyl ($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups, or an analog of such cycloalkyl group wherein one to three ring methylene groups are independently replaced by O, S, CHOH, >C═O, >C═S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_m C(O)N(R_{21})$— or $R_{26}C(O)(CH_2)_m N(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, S(O)$_m$ and wherein said alkynyl group is optionally independently substituted with one to two oxo groups, pyrrolidinyl, pyrrolyl, morpholinyl, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl)amino optionally substituted by one or more halogen atoms; or aroyl;

$R_6$ is:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently: nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}$, $R_{23}$ and $R_{24}$ is independently:

hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino;

or $R_{23}$ and $R_{24}$ taken together optionally form a heterocyclic or heteroaryl ring;

m=0, 1 or 2;

W is O or S and the pharmaceutically acceptable derivatives thereof.

A preferred subgeneric aspect of the invention comprises a method of using the compounds of the formula(II) as provided above and wherein:

G is:

phenyl, naphthyl, benzocyclobutanyl, dihydronaphthyl, tetrahydronaphthyl, benzocycloheptanyl, benzocycloheptenyl, indanyl, indenyl;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, indolinyl, indolonyl, indolinonyl, phthalimidyl;

oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl;

wherein G is substituted by one or more $R_1$, $R_2$ or $R_3$;

A more preferred subgeneric aspect of the invention comprises a method of using the compounds of the formula (II) as provided above and wherein:

G is phenyl, pyridinyl, pyridonyl, naphthyl, quinolinyl, isoquinolinyl, pyrazinyl, benzimidazolyl, benzoxazolyl, benzofuranyl, benzothiophenyl, benzpyrazolyl, dihydrobenzofuranyl, dihydrobenzothiophenyl, indanyl, indenyl, indolyl, indolinyl, indolonyl or indolinonyl, wherein G is substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl Y is:

a bond or a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:

phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, amino, mono- or di-($C_{1-3}$ alkyl)amino, $CONH_2$, or OH; nitrile, $C_{1-6}$ alkyl-$S(O)_m$, halogen, hydroxy, $C_{1-4}$ alkoxy, amino, mono- or di-($C_{1-6}$ alkyl)amino, mono- or di-($C_{1-3}$ alkyl) aminocarbonyl or $NH_2C(O)$;

each $R_1$ is independently:

$C_{3-6}$ alkyl optionally partially or fully halogenated, and optionally substituted with one to three $C_{3-6}$cycloalkyl, phenyl, thienyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile or $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; or an analog of such cycloalkyl group wherein one to three ring methylene groups are independently replaced by O, S, CHOH, >C=O, >C=S or NH; or silyl containing three $C_{1-4}$ alkyl groups optionally partially or fully halogenated;

$R_2$ is independently:

halogen, $C_{1-3}$ alkoxy, $C_{1-3}$ alkyl-$S(O)_m$ optionally partially or fully halogenated, phenylsulfonyl or nitrile;

$R_3$ is independently:

phenyl, morpholino, pyridinyl, pyrimidinyl, pyrazinyl, pyrrolyl, pyrrolylidinyl, imidazolyl, pyrazolyl, each being optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$alkyl, halogen, oxo, hydroxy, nitrile, $C_{1-3}$ alkyloxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl)aminocarbonyl, $C_{1-5}$ alkyl-$C(O)$—$C_{1-4}$ alkyl, mono- or di-($C_{1-3}$alkyl)amino, mono- or di-($C_{1-3}$)alkylamino-$C_{1-5}$ alkyl, mono- or di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl ($R_{11}$)N, carboxy-mono- or di-($C_{1-5}$)-alkylamino;

$C_{1-3}$ alkyl or $C_{1-4}$ alkoxy each being optionally partially or fully halogenated or optionally substituted with $R_{17}$;

$OR_{18}$ or $C_{1-6}$ alkyl optionally substituted with $OR_{18}$;

amino or mono- or di-($C_{1-5}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$alkenyl substituted by $R_{23}R_{24}NC(O)$—; or $C_{2-4}$ alkynyl branched or unbranched carbon chain optionally partially or fully halogenated and optionally independently substituted with one to two oxo groups, pyrroldinyl, pyrrolyl, morpholinyl, piperidinyl, piperazinyl, imidazolyl, phenyl, pyridinyl, tetrazolyl or one or more $C_{1-4}$ alkyl optionally substituted by one or more halogen atoms; and $R_{23}$ and $R_{24}$ taken together optionally form imidazolyl, piperidinyl, morpholinyl, piperazinyl or a pyridinyl ring.

A yet more preferred subgeneric aspect of the invention comprises a method of using the compounds of the formula (II), as described in the immediate previous paragraph, wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl or indolinonyl, wherein G is substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated carbon chain wherein one of the carbon atoms is optionally replaced by O, N or S and wherein Y is optionally independently substituted with an oxo group;

Z is:

phenyl, pyridinyl, pyrimidinyl, pyridazinyl, pyrazinyl, imidazolyl, dihydrothiazolyl, dihydrothiazolyl sulfoxide, pyranyl or pyrrolidinyl which are optionally substituted with one to two $C_{1-2}$ alkyl or $C_{1-2}$ alkoxy;

tetrahydropyranyl, morpholinyl, thiomorpholinyl, thiomorpholino sulfoxidyl, piperidinyl, piperidinonyl, piperazinyl or tetrahydropyrimidonyl which are optionally substituted with one to two $C_{1-2}$ alkyl or $C_{1-2}$ alkoxy; or $C_{1-3}$ alkoxy;

each $R_1$ is independently:

$C_{3-5}$ alkyl optionally partially or fully halogenated, and optionally substituted with phenyl substituted with zero to three halogen, $C_{1-3}$ alkyl which is optionally partially or fully halogenated, hydroxy, nitrile or $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O; and silyl containing three $C_{1-2}$ independently alkyl groups optionally partially or fully halogenated;

each $R_2$ is independently:

bromo, chloro, fluoro, methoxy, methylsulfonyl or nitrile;

each $R_3$ is independently:

phenyl, morpholino, pyridinyl, pyrimidinyl, pyrrolylidinyl, 2,5-pyrrolidin-dionyl, imidazolyl, pyrazolyl, each of the aforementioned is optionally substituted with one to three $C_{1-3}$ alkyl which is optionally partially or fully halogenated, halogen, oxo, hydroxy, nitrile and $C_{1-3}$ alkyloxy optionally partially or fully halogenated;

$C_{1-3}$ alkyl or $C_{1-3}$ alkoxy each being optionally partially or fully halogenated or optionally substituted with $R_{17}$;

$OR_{18}$ or $C_{1-3}$ alkyl optionally substituted with $OR_{18}$;

amino or mono- or di-($C_{1-3}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl; and $R_{23}$ and $R_{24}$ taken together optionally form morpholino.

A yet further preferred subgeneric aspect of the invention comprises a method of using the compounds of the formula (II), as described in the immediate previous paragraph, and wherein:

G is phenyl, pyridinyl, pyridonyl, naphthyl, quinolinyl, isoquinolinyl, dihydrobenzofuranyl, indanyl, indolinyl, indolonyl, or indolinonyl, wherein G is substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or

—$CH_2$—, —$CH_2CH_2$—, —C(O)—, —O—, —S—, —NH—$CH_2CH_2CH_2$—, —N($CH_3$)—, or —NH—;

each $R_1$ is independently:

$C_{3-5}$ alkyl optionally partially or fully halogenated, and optionally substituted with phenyl;

cyclopropyl, cyclopentanyl, cyclohexanyl and bicyclopentanyl optionally substituted with one to three methyl groups optionally partially or fully halogenated, CN, hydroxymethyl or phenyl; or 2-tetrahydrofuranyl substituted by methyl; or trimethyl silyl;

each $R_3$ is independently:

phenyl, morpholinyl, pyridinyl, pyrimidinyl, pyrrolylidinyl, 2,5-pyrrolidin-dionyl, imidazolyl or pyrazolyl, wherein any of the aforementioned is optionally substituted with $C_{1-2}$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$alkenyl substituted by $R_{23}R_{24}NC(O)$—; or $C_{2-4}$ alkynyl substituted with pyrroldinyl or pyrrolyl;

$R_{23}$ and $R_{24}$ are H or $R_{23}$ and $R_{24}$ taken together optionally form morpholino; and $R_{26}$ is morpholino.

A further preferred subgeneric aspect of the invention comprises a method of using the compounds of the formula (II), as described in the immediate previous paragraph, and wherein:

G is phenyl, pyridinyl or naphthyl wherein G is substituted by one or more $R_1$, $R_2$ or $R_3$;

X is:

imidazolyl or pyridinyl;

Y is:

—$CH_2$—, —NH—$CH_2CH_2CH_2$— or —NH—;

Z is morpholino;

each $R_1$ is independently:

tert-butyl, sec-butyl, tert-amyl or phenyl;

$R_2$ is chloro;

$R_3$ is independently:

methyl, methoxy, methoxymethyl, hydroxypropyl, acetamide, morpholino or morpholinocarbonyl.

A still yet further preferred subgeneric aspect of the invention comprises a method of using the compounds of the formula (II), as described in the immediate previous paragraph, and wherein X is pyridinyl.

A still yet further preferred subgeneric aspect of the invention comprises a method of using the compounds of the formula (II), as described immediately above, and wherein the pyridinyl is attached to Ar via the 3-pyridinyl position.

The following compounds are representative of the compounds of formula(II) which are useful in the novel methods described herein:

1-(3-Cyano-phenyl)-3-[4-(6-morpholin-4-ylmethyl-pyridin-3-yl)-naphthalen-1-yl]-urea;

1-(3-Fluoro-phenyl)-3-[4-(6-morpholin-4-ylmethyl-pyridin-3-yl)-naphthalen-1-yl]-urea;

1-(4-Chloro-2-trifluoromethyl-phenyl)-3-[4-(6-morpholin-4-ylmethyl-pyridin-3-yl)-naphthalen-1-yl]-urea;

1-(2-Chloro-5-trifluoromethyl-phenyl)-3-[4-(6-morpholin-4-ylmethyl-pyridin-3-yl)-naphthalen-1-yl]-urea;

1-(3,4-Dimethyl-phenyl)-3-[4-(6-morpholin-4-ylmethyl-pyridin-3-yl)-naphthalen-1-yl]-urea;

1-(3-Iodo-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-m-tolyl-urea;

1-(4-Methylsulfanyl-phenyl)-3-[4-(6-morpholin-4-ylmethyl-pyridin-3-yl)-naphthalen-1-yl]-urea;

1-(3-Chloro-4-methyl-phenyl)-3-[4-(6-morpholin-4-ylmethyl-pyridin-3-yl)-naphthalen-1-yl]-urea;

1-(4-Chloro-3-nitro-phenyl)-3-[4-(6-morpholin-4-ylmethyl-pyridin-3-yl)-naphthalen-1-yl]-urea;

1-(2,5-Dichloro-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-naphthalen-2-yl-urea;

1-[4-(6-Morpholin-4-ylmethyl-pyridin-3-yl)-naphthalen-1-yl]-3-phenyl-urea;
1-(3-Chloro-phenyl)-3-[4-(6-morpholin-4-ylmethyl-pyridin-3-yl)-naphthalen-1-yl]-urea;
1-(4-Chloro-3-trifluoromethyl-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(2,4,6-trichloro-phenyl)-urea;
1-(2-Methyl-3-nitro-phenyl)-3-[4-(6-morpholin-4-ylmethyl-pyridin-3-yl)-naphthalen-1-yl]-urea;
1-(4-Methyl-2-nitro-phenyl)-3-[4-(6-morpholin-4-ylmethyl-pyridin-3-yl)-naphthalen-1-yl]-urea;
1-(2,3-Dichloro-phenyl)-3-[4-(6-morpholin-4-ylmethyl-pyridin-3-yl)-naphthalen-1-yl]-urea;
1-(2-Methoxy-5-methyl-phenyl)-3-[4-(6-morpholin-4-ylmethyl-pyridin-3-yl)-naphthalen-1-yl]-urea;
1-(2-Chloro-6-methyl-phenyl)-3-[4-(6-morpholin-4-ylmethyl-pyridin-3-yl)-naphthalen-1-yl]-urea;
1-(2,4-Dichloro-phenyl)-3-[4-(6-morpholin-4-ylmethyl-pyridin-3-yl)-naphthalen-1-yl]-urea;
1-(4-Methyl-3-nitro-phenyl)-3-[4-(6-morpholin-4-ylmethyl-pyridin-3-yl)-naphthalen-1-yl]-urea;
1-(2,4-Dimethyl-phenyl)-3-[4-(6-morpholin-4-ylmethyl-pyridin-3-yl)-naphthalen-1-yl]-urea;
1-(2,3-Dimethyl-phenyl)-3-[4-(6-morpholin-4-ylmethyl-pyridin-3-yl)-naphthalen-1-yl]-urea;
1-(4-Cyano-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3,4,5-trimethoxy-phenyl)-urea;
1-Biphenyl-4-yl-3-[4-(6-morpholin-4-ylmethyl-pyridin-3-yl)-naphthalen-1-yl]-urea;
1-(2,5-Difluoro-phenyl)-3-[4-(6-morpholin-4-ylmethyl-pyridin-3-yl)-naphthalen-1-yl]-urea;
1-(3-Chloro-2-methoxy-phenyl)-3-[4-(6-morpholin-4-ylmethyl-pyridin-3-yl)-naphthalen-1-yl]-urea;
1-(2-Fluoro-3-trifluoromethyl-phenyl)-3-[4-(6-morpholin-4-ylmethyl-pyridin-3-yl)-naphthalen-1-yl]-urea;
1-(4-Benzyloxy-phenyl)-3-[4-(6-morpholin-4-ylmethyl-pyridin-3-yl)-naphthalen-1-yl]-urea;
1-(2-Methylsulfanyl-phenyl)-3-[4-(6-morpholin-4-ylmethyl-pyridin-3-yl)-naphthalen-1-yl]-urea;
1-(2-Fluoro-6-trifluoromethyl-phenyl)-3-[4-(6-morpholin-4-ylmethyl-pyridin-3-yl)-naphthalen-1-yl]-urea;
1-(4-Fluoro-3-trifluoromethyl-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(2,4,5-trimethyl-phenyl)-urea;
1-[4-(6-Morpholin-4-ylmethyl-pyridin-3-yl)-naphthalen-1-yl]-3-(4-trifluoromethyl-phenyl)-urea;
1-(3-Methylsulfanyl-phenyl)-3-[4-(6-morpholin-4-ylmethyl-pyridin-3-yl)-naphthalen-1-yl]-urea;
1-(2-Methoxy-phenyl)-3-[4-(6-morpholin-4-ylmethyl-pyridin-3-yl)-naphthalen-1-yl]-urea;
1-(2-Fluoro-5-trifluoromethyl-phenyl)-3-[4-(6-morpholin-4-ylmethyl-pyridin-3-yl)-naphthalen-1-yl]-urea;
1-(4-Methoxy-2-methyl-phenyl)-3-[4-(6-morpholin-4-ylmethyl-pyridin-3-yl)-naphthalen-1-yl]-urea;
1-(2-Fluoro-5-nitro-phenyl)-3-[4-(6-morpholin-4-ylmethyl-pyridin-3-yl)-naphthalen-1-yl]-urea;
1-(4-Ethoxy-phenyl)-3-[4-(6-morpholin-4-ylmethyl-pyridin-3-yl)-naphthalen-1-yl]-urea;
1-(2,5-Dimethoxy-phenyl)-3-[4-(6-morpholin-4-ylmethyl-pyridin-3-yl)-naphthalen-1-yl]-urea;
b 1-(4,5-Dimethyl-2-nitro-phenyl)-3-[4-(6-morpholin-4-ylmethyl-pyridin-3-yl)-naphthalen-1-yl]-urea;
1-(5-Chloro-2-methyl-phenyl)-3-[4-(6-morpholin-4-ylmethyl-pyridin-3-yl)-naphthalen-1-yl]-urea;
1-(2-Isopropyl-6-methyl-phenyl)-3-[4-(6-morpholin-4-ylmethyl-pyridin-3-yl)-naphthalen-1-yl]-urea;
1-(2-Difluoromethoxy-phenyl)-3-[4-(6-morpholin-4-ylmethyl-pyridin-3-yl)-naphthalen-1-yl]-urea;
1-(4-Isopropyl-phenyl)-3-[4-(6-morpholin-4-ylmethyl-pyridin-3-yl)-naphthalen-1-yl]-urea;
1-(4-Methoxy-phenyl)-3-[4-(6-morpholin-4-ylmethyl-pyridin-3-yl)-naphthalen-1-yl]-urea;
1-(3-Ethyl-phenyl)-3-[4-(6-morpholin-4-ylmethyl-pyridin-3-yl)-naphthalen-1-yl]-urea;
1-(2-Ethoxy-phenyl)-3-[4-(6-morpholin-4-ylmethyl-pyridin-3-yl)-naphthalen-1-yl]-urea;
1-(4-Butoxy-phenyl)-3-[4-(6-morpholin-4-ylmethyl-pyridin-3-yl)-naphthalen-1-yl]-urea;
4-{3-[4-(6-Morpholin-4-ylmethyl-pyridin-3-yl)-naphthalen-1-yl]-ureido}-benzoic acid ethyl ester;
1-(4-Butyl-2-methyl-phenyl)-3-[4-(6-morpholin-4-ylmethyl-pyridin-3-yl)-naphthalen-1-yl]-urea;
1-(2,6-Dibromo-4-isopropyl-phenyl)-3-[4-(6-morpholin-4-ylmethyl-pyridin-3-yl)-naphthalen-1-yl]-urea;
1-(3-Methoxy-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(4-trifluoromethylsulfanyl-phenyl)-urea;
5-{3-[4-(6-Morpholin-4-ylmethyl-pyridin-3-yl)-naphthalen-1-yl]-ureido}-isophthalic acid dimethyl ester;
1-(3-Cyclopentyloxy-4-methoxy-phenyl)-3-[4-(6-morpholin-4-ylmethyl-pyridin-3-yl)-naphthalen-1-yl]-urea;
3-{3-[4-(6-Morpholin-4-ylmethyl-pyridin-3-yl)-naphthalen-1-yl]-ureido}-benzoic acid ethyl ester;
1-(5-tert-Butyl-2-hydroxy-phenyl)-3-[4-(6-morpholin-4-ylmethyl-pyridin-3-yl)-naphthalen-1-yl]-urea;
1-(2-Hydroxymethyl-4-phenyl-cyclohexyl)-3-[4-(6-morpholin-4-ylmethyl-pyridin-3-yl)-naphthalen-1-yl]-urea;
1-(2-Methylsulfanyl-5-trifluoromethyl-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(4-pentyloxy-biphenyl-3-yl)-urea;
4-Methoxy-3-{3-[4-(6-morpholin-4-ylmethyl-pyridin-3-yl)-naphthalen-1-yl]-ureido}-benzoic acid methyl ester;
1-(2,5-Diethoxy-phenyl)-3-[4-(6-morpholin-4-ylmethyl-pyridin-3-yl)-naphthalen-1-yl]-urea;
1-Benzothiazol-6-yl-3-[4-(6-morpholin-4-ylmethyl-pyridin-3-yl)-naphthalen-1-yl]-urea;
N-(2,5-Diethoxy-4-{3-[4-(6-morpholin-4-ylmethyl-pyridin-3-yl)-naphthalen-1-yl]-ureido}-phenyl)-benzamide;
1-[4-(6-Morpholin-4-ylmethyl-pyridin-3-yl)-naphthalen-1-yl]-3-(3-phenoxy-phenyl)-urea;
1-(5-Ethanesulfonyl-2-methoxy-phenyl)-3-[4-(6-morpholin-4-ylmethyl-pyridin-3-yl)-naphthalen-1-yl]-urea;
4-Methoxy-3-{3-[4-(6-morpholin-4-ylmethyl-pyridin-3-yl)-naphthalen-1-yl]-ureido}-N-phenyl-benzamide;
1-(2-Methyl-1,3-dioxo-2,3-dihydro-1H-isoindol-5-yl)-3-[4-(6-morpholin-4-ylmethyl-pyridin-3-yl)-naphthalen-1-yl]-urea;
1-(2,3-Dimethyl-1H-indol-5-yl)-3-[4-(6-morpholin-4-ylmethyl-pyridin-3-yl)-naphthalen-1-yl]-urea;
N-Butyl-4-methoxy-3-{3-[4-(6-morpholin-4-ylmethyl-pyridin-3-yl)-naphthalen-1-yl]-ureido}-benzenesulfonamide;
1-[3-(2-Methyl-[1,3]dioxolan-2-yl)-phenyl]-3-[4-(6-morpholin-4-ylmethyl-pyridin-3-yl)-naphthalen-1-yl]-urea;
1-(3-Methoxy-5-trifluoromethyl-phenyl)-3-[4-(6-morpholin-4-ylmethyl-pyridin-3-yl)-naphthalen-1-yl]-urea;

1-(2,4-Dimethoxy-phenyl)-3-[4-(6-morpholin-4-ylmethyl-pyridin-3-yl)-naphthalen-1-yl]-urea;
1-(2-Methyl-4-nitro-phenyl)-3-[4-(6-morpholin-4-ylmethyl-pyridin-3-yl)-naphthalen-1-yl]-urea;
1-(2-Methoxy-4-nitro-phenyl)-3-[4-(6-morpholin-4-ylmethyl-pyridin-3-yl)-naphthalen-1-yl]-urea;
1-(4-Chloro-2-nitro-phenyl)-3-[4-(6-morpholin-4-ylmethyl-pyridin-3-yl)-naphthalen-1-yl]-urea;
1-(5-Chloro-2-methoxy-phenyl)-3-[4-(6-morpholin-4-ylmethyl-pyridin-3-yl)-naphthalen-1-yl]-urea;
1-(3,5-Dimethoxy-phenyl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(4-trifluoromethoxy-phenyl)-urea;
1-[4-(6-Morpholin-4-ylmethyl-pyridin-3-yl)-naphthalen-1-yl]-3-(3-trifluoromethylsulfanyl-phenyl)-urea;
1-[4-(6-Morpholin-4-ylmethyl-pyridin-3-yl)-naphthalen-1-yl]-3-(2-phenoxy-phenyl)-urea;
1-(2-Methoxy-5-nitro-phenyl)-3-[4-(6-morpholin-4-ylmethyl-pyridin-3-yl)-naphthalen-1-yl]-urea;
1-(5-Chloro-2,4-dimethoxy-phenyl)-3-[4-(6-morpholin-4-ylmethyl-pyridin-3-yl)-naphthalen-1-yl]-urea;
1-(3,5-Bis-trifluoromethyl-phenyl)-3-[4-(6-morpholin-4-ylmethyl-pyridin-3-yl)-naphthalen-1-yl]-urea;
1-(2-tert-Butyl-5-methyl-pyridin-4-yl)-3-[4-(6-morpholin-4-ylmethyl-pyridin-3-yl)-naphthalen-1-yl]-urea;
1-(3-Methyl-naphthalen-2-yl)-3-[4-(6-morpholin-4-ylmethyl-pyridin-3-yl)-naphthalen-1-yl]-urea;
1-(3-tert-Butyl-phenyl)-3-[4-(6-morpholin-4-ylmethyl-pyridin-3-yl)-naphthalen-1-yl]-urea;
1-(4-Methyl-biphenyl-3-yl)-3-[4-(6-morpholin-4-ylmethyl-pyridin-3-yl)-naphthalen-1-yl]-urea;
1-(4-tert-Butyl-biphenyl-2-yl)-3-[4-(6-morpholin-4-ylmethyl-pyridin-3-yl)-naphthalen-1-yl]-urea;
1-(5-Chloro-2,4-dimethoxy-phenyl)-3-[4-(6-morpholin-4-ylmethyl-pyridin-3-yl)-naphthalen-1-yl]-urea;
1-(5-Isopropyl-2-methyl-phenyl)-3-[4-(6-morpholin-4-ylmethyl-pyridin-3-yl)-naphthalen-1-yl]-urea;
1-(5-sec-Butyl-2-methoxy-phenyl)-3-[4-(6-morpholin-4-ylmethyl-pyridin-3-yl)-naphthalen-1-yl]-urea;
1-(5-tert-Butyl-2-methoxy-3-propyl-phenyl)-3-[4-(6-morpholin-4-ylmethyl-pyridin-3-yl)-naphthalen-1-yl]-urea;
1-(5-tert-Butyl-2-methoxymethyl-phenyl)-3-[4-(6-morpholin-4-ylmethyl-pyridin-3-yl)-naphthalen-1-yl]-urea;
1-(5-tert-Butyl-2-methoxy-phenyl)-3-[4-(6-morpholin-4-ylmethyl-pyridin-3-yl)-naphthalen-1-yl]-urea;
1-(5-tert-Butyl-2-methyl-phenyl)-3-(4-{6-[(3-methoxy-propyl)-methyl-amino]-pyridin-3-yl}-naphthalen-1-yl)-urea;
1-(5-tert-Butyl-2-methyl-phenyl)-3-[4-(4-morpholin-4-ylmethyl-imidazol-1-yl)-naphthalen-1-yl]urea;
1-(5-tert-Butyl-2-methyl-phenyl)-3-[4-(6-morpholin-4-ylmethyl-pyridin-3-yl)-naphthalen-1-yl]-urea;
1-(5-tert-Butyl-2-methyl-phenyl)-3-{4-[6-(3-methoxy-propylamino)-pyridin-3-yl]-naphthalen-1-yl}-urea;
1-(5-tert-Butyl-2-methyl-pyridin-3-yl)-3-[4-(6-morpholin-4-ylmethyl-pyridin-3-yl)-naphthalen-1-yl]-urea;
1-(5-tert-Butyl-2-morpholin-4-yl-phenyl)-3-[4-(6-morpholin-4-ylmethyl-pyridin-3-yl)-naphthalen-1-yl]-urea;
1-(6-tert-Butyl-2-chloro-3-methyl-pyridin-4-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3-trifluoromethyl-phenyl)-urea;
1-[4-(6-Morpholin-4-ylmethyl-pyridin-3-yl)-naphthalen-1-yl]-3-(4-trifluoromethoxy-phenyl)-urea;
1-[5-(1,1-Dimethyl-propyl)-2-methoxy-phenyl]-3-[4-(6-morpholin-4-ylmethyl-pyridin-3-yl)-naphthalen-1-yl]-urea;
1-[5-tert-Butyl-2-(1H-pyrazol-4-yl)-phenyl]-3-[4-(6-morpholin-4-ylmethyl-pyridin-3-yl)-naphthalen-1-yl]-urea;
1-[5-tert-Butyl-2-(2-methyl-pyrimidin-5-yl)-phenyl]-3-[4-(6-morpholin-4-ylmethyl-pyridin-3-yl)-naphthalen-1-yl]-urea;
1-[5-tert-Butyl-2-(3-hydroxy-propyl)-phenyl]-3-[4-(6-morpholin-4-ylmethyl-pyridin-3-yl)-naphthalen-1-yl]-urea;
1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea;
1-[5-tert-Butyl-2-(morpholine-4-carbonyl)-phenyl]-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen--1-yl]-ureido}-phenyl)-acetamide;
2-(5-tert-Butyl-2-methoxy-phenyl)-N-[4-(6-morpholin-4-ylmethyl-pyridin-3-yl)-naphthalen-1-yl]-acetamide;
1-(3-Amino-5-tert-butyl-2-methoxy-phenyl)-3-[4-(6-methyl-pyridin-3-yl)-naphthalen-1-yl]-urea;
1-(5-tert-Butyl-2-ethoxy-phenyl)-3-[4-(6-morpholin-4-ylmethyl-pyridin-3-yl)-naphthalen-1-yl]-urea;
N-(5-tert-Butyl-2-methoxy-4-{3-[4-(6-morpholin-4-ylmethyl-pyridin-3-yl)-naphthalen-1-yl]-ureido}-phenyl)-methanesulfonamide;
1-(5-tert-Butyl-2-methoxy-phenyl)-3-[4-(4-morpholin-4-ylmethyl-piperidin-1-yl)-naphthalen-1-yl]-urea;
1-(5-tert-Butyl-2-methoxy-phenyl)-3-[4-(2-morpholin-4-ylmethyl-pyrimidin-5-yl)-naphthalen-1-yl]-urea;
1-(5-tert-Butyl-2-methoxy-pyridin-3-yl)-3-[4-(6-morpholin-4-ylmethyl-pyridin-3-yl)-naphthalen-1-yl]-urea;
2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide and the pharmaceutically acceptable derivatives thereof.

In addtion to the abovementioned representative compounds the following prophetic compounds of the formula (II) may be useful in the novel methods described herein:

1-[4-(6-{[Bis-(2-cyano-ethyl)-amino]-methyl}-pyridin-3-yl)-naphthalen-1-yl]-3-(5-tert-butyl-2-methoxy-phenyl)-urea
1-(5-tert-Butyl-2-methoxy-phenyl)-3-{4-[4-(2-methyl-3-oxo-piperazin-1-ylmethyl)-phenyl]-naphthalen-1-yl}-urea
1-[4-(6-{[Bis-(2-methoxy-ethyl)-amino]-methyl}-pyridin-3-yl)-naphthalen-1-yl]-3-(5-tert-butyl-2-methoxy-phenyl)-urea
1-(5-tert-Butyl-2-methoxy-phenyl)-3-{4-[6-(2-methyl-3-oxo-piperazin-1-ylmethyl)-pyridin-3-yl]-naphthalen-1-yl}-urea;
1-(5-tert-Butyl-2-methoxy-phenyl)-3-{4-[6-(1-oxo-114-thiomorpholin-4-ylmethyl)-pyridin-3-yl]-naphthalen-1-yl}-urea;
1-(5-tert-Butyl-2-methoxy-phenyl)-3-[4-(6-thiomorpholin-4-ylmethyl-pyridin-3-yl)-naphthalen-1-yl]-urea;
1-(5-tert-Butyl-2-methyl-phenyl)-3-{4-[6-(1-oxo-114-thiomorpholin-4-ylmethyl)-pyridin-3-yl]-naphthalen-1-yl}-urea;
1-(5-tert-Butyl-2-methyl-phenyl)-3-{4-[6-(2-methyl-3-oxo-piperazin-1-ylmethyl)-pyridin-3-yl]-naphthalen-1-yl}-urea;
1-(5-tert-Butyl-2-methoxy-phenyl)-3-{4-[4-(1-oxo-11-thiomorpholin-4-ylmethyl)-phenyl]-naphthalen-1-yl}-urea;

1-[4-(4-{[Bis-(2-cyano-ethyl)-amino]-methyl}-phenyl)-naphthalen-1-yl]-3-(5-tert-butyl-2-methoxy-phenyl)-urea;

1-(2-Methoxy-5-pentafluoroethyl-phenyl)-3-[4-(4-morpholin-4-ylmethyl-piperidin-1-yl)-naphthalen-1-yl]-urea;

1-(2-Methoxy-5-trifluoromethyl-pyridin-3-yl)-3-{4-[2-(4-oxo-piperidin-1-ylmethyl)-pyrimidin-5-yl]-naphthalen-1-yl}-urea;

1-(2-Methoxy-5-trimethylsilanyl-phenyl)-3-{4-[4-(tetrahydro-pyran-4-ylamino)-phenyl]-naphthalen-1-yl}-urea;

1-(3-Methoxy-naphthalen-2-yl)-3-[4-(4-morpholin-4-ylmethyl-piperidin-1-yl)-naphthalen-1-yl]-urea;

1-(3-Methyl-naphthalen-2-yl)-3-[4-(4-morpholin-4-ylmethyl-phenyl)-naphthalen-1-yl]-urea 1-(3-tert-Butyl-5-methanesulfinyl-phenyl)-3-{4-[6-(1-methyl-piperidin-4-ylmethyl)-pyridin-3-yl]-naphthalen-1-yl}-urea;

1-(3-tert-Butyl-phenyl)-3-[4-(3-pyridin-3-yl-propoxy)-naphthalen-1-yl]-urea;

1-(3-tert-Butyl-phenyl)-3-[4-(4-morpholin-4-ylmethyl-phenyl)-naphthalen-1-yl]-urea;

1-(4-Methoxy-biphenyl-3-yl)-3-{4-[4-(tetrahydro-pyran-4-ylmethyl)-imidazol-1-yl]-naphthalen-1-yl}-urea;

1-(4-Methyl-biphenyl-3-yl)-3-{4-[4-(2-pyridin-4-yl-ethyl)-piperazin-1-yl]-naphthalen-1-yl}-urea;

1-(4-tert-Butyl-biphenyl-2-yl)-3-[4-(pyridin-4-ylmethoxy)-naphthalen-1-yl]-urea;

1-(4-tert-Butyl-biphenyl-2-yl)-3-{4-[2-(1-oxo-1λ4-thiomorpholin-4-ylmethyl)-3H-imidazol-4-yl]-naphthalen-1-yl}-urea;

1-(5-tert-Butyl-2-hydroxy-phenyl)-3-[4-(5-morpholin-4-ylmethyl-pyrazin-2-yl)-naphthalen-1-yl]-urea;

1-(5-tert-Butyl-2-methoxy-3-propyl-phenyl)-3-{4-[4-(pyrrolidine-1-carbonyl)-phenyl]-naphthalen-1-yl}-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methoxy-phenyl)-3-[4-(4-thiomorpholin-4-ylmethyl-phenyl)-naphthalen-1-yl]-urea;

1-(5-tert-Butyl-2-methoxy-phenyl)-3-[4-(6-morpholin-4-ylmethyl-phenyl)-naphthalen-1-yl]-urea;

1-(5-tert-Butyl-2-methoxy-phenyl)-3-{4-[4-(tetrahydro-pyran-4-ylamino)-phenyl]-naphthalen-1-yl}-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-pyridin-3-yl)-3-{4-[6-(4-oxo-piperidin-1-ylmethyl)-pyridin-3-yl]-naphthalen-1-yl}-urea;

1-(5-tert-Butyl-2-methyl-benzooxazol-7-yl)-3-[4-(6-pyridin-4-ylmethyl-pyridin-3-yl)-naphthalen-1-yl]-urea;

1-(5-tert-Butyl-2-methyl-phenyl)-3-[4-(4-morpholin-4-ylmethyl-phenyl)-naphthalen-1-yl]-urea;

1-(5-tert-Butyl-2-phenoxy-phenyl)-3-{4-[6-(tetrahydro-pyran-4-yloxy)-pyridin-3-yl]-naphthalen-1-yl}-urea;

1-(5-tert-Butyl-2-pyrrolidin-1-yl-phenyl)-3-[4-(4-methoxy-6-morpholin-4-ylmethyl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-3-cyano-2-methoxy-phenyl)-3-{4-[2-(2,6-dimethyl-morpholin-4-ylmethyl)-pyrimidin-5-yl]-naphthalen-1-yl}-urea;

1-(5-tert-Butyl-4'-dimethylamino-biphenyl-3-yl)-3-[4-(2-morpholin-4-ylmethyl-pyrimidin-5-yl)-naphthalen-1-yl]-urea;

1-(6-Methoxy-3,3-dimethyl-indan-5-yl)-3-{4-[4-(morpholine-4-carbonyl)-phenyl]-naphthalen-1-yl}-urea;

1-(6-tert-Butyl-2-chloro-3-methyl-pyridin-4-yl)-3-[4-(6-thiomorpholin-4-ylmethyl-pyridin-3-yl)-naphthalen-1-yl]-urea;

1-(6-tert-Butyl-benzo[1,3]dioxol-4-yl)-3-{4-[6-(morpholin-4-ylamino)-pyridin-3-yl]-naphthalen-1-yl}-urea;

1-(7-Methoxy-1,4,4-trimethyl-1,2,3,4-tetrahydro-quinolin-6-yl)-3-{4-[6-(tetrahydro-pyran-4-yloxy)-pyridin-3-yl]-naphthalen-1-yl}-urea;

1-(7-tert-Butyl-2,4-dimethyl-benzooxazol-5-yl)-3-[4-(6-morpholin-4-ylmethyl-pyridin-3-yl)-naphthalen-1-yl]-urea;

1-[2-Methoxy-5-(1-methyl-1-phenyl-ethyl)-phenyl]-3-{4-[6-(2-pyridin-4-yl-ethyl)-pyridazin-3-yl]-naphthalen-1-yl}-urea;

1-[2-Methoxy-5-(1-methyl-cyclohexyl)-phenyl]-3-{4-[4-(1-methyl-piperidin-4-ylsulfanyl)-phenyl]-naphthalen-1-yl}-urea;

1-[2-Methoxy-5-(1-methyl-cyclopropyl)-phenyl]-3-[4-(2-morpholin-4-ylmethyl-pyrimidin-5-yl)-naphthalen-1-yl]-urea;

1-[2-Methoxy-5-(2-methyl-tetrahydro-furan-2-yl)-phenyl]-3-[4-(5-morpholin-4-ylmethyl-pyridin-2-yl)-naphthalen-1-yl]-urea;

1-[2-Methoxy-5-(3-trifluoromethyl-bicyclo[1.1.1]pent-1-yl)-phenyl]-3-[4-(4-morpholin-4-ylmethyl-phenyl)-naphthalen-1-yl]-urea;

1-[3-tert-Butyl-5-(1-methyl-1H-imidazol-4-yl)-phenyl]-3-[4-(5-morpholin-4-ylmethyl-pyridin-2-yl)-naphthalen-1-yl]-urea;

1-[3-tert-Butyl-5-(2-pyrrolidin-1-yl-ethyl)-phenyl]-3-{4-[6-(1-methyl-piperidin-4-yloxy)-pyridin-3-yl]-naphthalen-1-yl}-urea;

1-[3-tert-Butyl-5-(3-pyrrolidin-1-yl-prop-1-ynyl)-phenyl]-3-[4-(6-morpholin-4-ylmethyl-pyridin-3-yl)-naphthalen-1-yl]-urea;

1-[4-(6-Imidazol-1-ylmethyl-pyridin-3-yl)-naphthalen-1-yl]-3-[2-methoxy-5-(1-phenyl-cyclopropyl)-phenyl]-urea;

1-[5-(1,1-Dimethyl-propyl)-2-methoxy-phenyl]-3-[4-(4-thiomorpholin-4-ylmethyl-phenyl)-naphthalen-1-yl]-urea;

1-[5-(1-Cyano-cyclopropyl)-2-methoxy-phenyl]-3-[4-(2-morpholin-4-ylmethyl-pyrimidin-5-yl)-naphthalen-1-yl]-urea;

1-[5-(1-Hydroxymethyl-cyclopropyl)-2-methoxy-phenyl]-3-[4-(4-morpholin-4-ylmethyl-phenyl)-naphthalen-1-yl]-urea;

1-[5-tert-Butyl-1-(2-diethylamino-ethyl)-2-oxo-1,2-dihydro-pyridin-3-yl]-3-{4-[6-(1-methyl-piperidin-4-yloxy)-pyridin-3-yl]-naphthalen-1-yl}-urea;

1-[5-tert-Butyl-2-(1H-pyrazol-4-yl)-phenyl]-3-[4-(2-morpholin-4-yl-ethoxy)-naphthalen-1-yl]-urea;

1-[5-tert-Butyl-2-(1H-pyrazol-4-yl)-phenyl]-3-{4-[4-(4-methyl-piperazine-1-carbonyl)-phenyl]-naphthalen-1-yl}-urea;

1-[5-tert-Butyl-2-(2,5-dioxo-pyrrolidin-1-yl)-phenyl]-3-{4-[6-(1H-imidazol-2-ylmethyl)-pyridin-3-yl]-naphthalen-1-yl}-urea;

1-[5-tert-Butyl-2-(2-methyl-pyrimidin-5-yl)-phenyl]-3-[4-(5-pyridin-4-ylmethyl-pyridin-2-yl)-naphthalen-1-yl]-urea;

1-[5-tert-Butyl-2-(2-morpholin-4-yl-2-oxo-ethoxy)-phenyl]-3-{4-[6-(2-pyridin-4-yl-ethyl)-pyridazin-3-yl]-naphthalen-1-yl}-urea;

1-[5-tert-Butyl-2-(2-morpholin-4-yl-2-oxo-ethylamino)-phenyl]-3-{4-[4-(1-methyl-piperidin-4-ylamino)-piperidin-1-yl]-naphthalen-1-yl}-urea;

1-[5-tert-Butyl-2-(6-methyl-pyridin-3-yl)-phenyl]-3-{4-[5-(2-pyrrolidin-1-yl-ethyl)-pyridin-2-yl]-naphthalen-1-yl}-urea;

1-[5-tert-Butyl-2-methoxy-3-(3-morpholin-4-yl-3-oxo-propenyl)-phenyl]-3-[4-(6-pyrrolidin-1-ylmethyl-pyridin-3-yl)-naphthalen-1-yl]-urea;

1-[5-tert-Butyl-3-(2-diethylamino-ethoxy)-2-methoxy-phenyl]-3-{4-[4-(tetrahydro-pyran-4-yloxy)-phenyl]-naphthalen-1-yl}-urea;

1-[5-tert-Butyl-3-(2-pyrrolidin-1-yl-ethyl)-benzofuran-7-yl]-3-[4-(4-morpholin-4-ylmethyl-phenyl)-naphthalen-1-yl]-urea;

1-[6-tert-Butyl-4-(2-dimethylamino-ethyl)-3-oxo-3,4-dihydro-2H-benzo[1,4]oxazin-8-yl]-3-{4-[6-(thiomorpholin-4-ylamino)-pyridin-3-yl]-naphthalen-1-yl}-urea;

1-{5-tert-Butyl-2-methoxy-3-[2-(1-methyl-piperidin-4-yloxy)-ethyl]-phenyl}-3-[4-(4-morpholin-4-ylmethyl-phenyl)-naphthalen-1-yl]-urea;

2-(4-tert-Butyl-2-{3-[4-(5-pyrrolidin-1-ylmethyl-pyridin-2-yl)-naphthalen-1-yl]-uriedo}-phenoxy)-N-methyl-acetamide;

2-[4-tert-Butyl-2-(3-{4-[6-(2,6-dimethyl-morpholin-4-ylmethyl)-pyridin-3-yl]-naphthalen-1-yl}-ureido)-phenoxy]-acetamide;

3-(5-tert-Butyl-2-methoxy-3-{3-[4-(6-pyrrolidin-1-ylmethyl-pyridin-3-yl)-naphthalen-1-yl]-ureido}-phenyl)-acrylamide;

3-{3-tert-Butyl-5-[3-(4-{4-[2-(1-oxo-114-thiazolidin-3-yl)-ethyl]-phenyl}-naphthalen-1-yl)-ureido]-phenyl}-N,N-dimethyl-propionamide;

3-{4-[3-(5-tert-Butyl-2-methoxy-phenyl)-ureido]-naphthalen-1-yl}-benzamide;

4-tert-Butyl-2-{3-[4-(2-chloro-4-morpholin-4-ylmethyl-phenyl)-naphthalen-1-yl]-ureido}-benzamide;

N-(4-tert-Butyl-2-{3-[4-(6-oxo-1,6-dihydro-pyridin-3-yl)-naphthalen-1-yl]-ureido}-phenyl)-2-morpholin-4-yl-acetamide;

N-[3-tert-Butyl-5-(3-{4-[5-(tetrahydro-pyran-4-ylamino)-pyridin-2-yl]-naphthalen-1-yl}-ureido)-phenyl]-2-morpholin-4-yl-acetamide;

N-[4-tert-Butyl-2-(3-{4-[4-(1-methyl-piperidin-4-yloxy)-phenyl]-naphthalen-1-yl}-ureido)-phenyl]-acetamide and the pharmaceutically acceptable derivatives thereof.

In another embodiment of the invention there are provided the following compounds of formula(II) which are useful in the novel methods described herein:

1-(2-tert-Butyl-5-methyl-pyridin-4-yl)-3-[4-(6-morpholin-4-ylmethyl-pyridin-3-yl)-naphthalen-1-yl]-urea;

1-(3-Methyl-naphthalen-2-yl)-3-[4-(6-morpholin-4-ylmethyl-pyridin-3-yl)-naphthalen-1-yl]-urea;

1-(3-tert-Butyl-phenyl)-3-[4-(4-morpholin-4-ylmethyl-phenyl)-naphthalen-1-yl]-urea;

1-(3-tert-Butyl-phenyl)-3-[4-(6-morpholin-4-ylmethyl-pyridin-3-yl)-naphthalen-1-yl]-urea;

1-(4-Methyl-biphenyl-3-yl)-3-[4-(6-morpholin-4-ylmethyl-pyridin-3-yl)-naphthalen-1-yl]-urea;

1-(4-tert-Butyl-biphenyl-2-yl)-3-[4-(6-morpholin-4-ylmethyl-pyridin-3-yl)-naphthalen-1-yl]-urea;

1-(5-Chloro-2,4-dimethoxy-phenyl)-3-[4-(6-morpholin-4-ylmethyl-pyridin-3-yl)-naphthalen-1-yl]-urea;

1-(5-Isopropyl-2-methyl-phenyl)-3-[4-(6-morpholin-4-ylmethyl-pyridin-3-yl)-naphthalen-1-yl]-urea;

1-(5-sec-Butyl-2-methoxy-phenyl)-3-[4-(6-morpholin-4-ylmethyl-pyridin-3-yl)-naphthalen-1-yl]-urea;

1-(5-tert-Butyl-2-methoxy-3-propyl-phenyl)-3-[4-(6-morpholin-4-ylmethyl-pyridin-3-yl)-naphthalen-1-yl]-urea;

1-(5-tert-Butyl-2-methoxymethyl-phenyl)-3-[4-(6-morpholin-4-ylmethyl-pyridin-3-yl)-naphthalen-1-yl]-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methoxy-phenyl)-3-[4-(4-thiomorpholin-4-ylmethyl-phenyl)-naphthalen-1-yl]-urea;

1-(5-tert-Butyl-2-methoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-morpholin-4-ylmethyl-phenyl)-naphthalen-1-yl]-urea;

1-(5-tert-Butyl-2-methoxy-phenyl)-3-{4-[4-(tetrahydro-pyran-4-ylamino)-phenyl]-naphthalen-1-yl}-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methyl-phenyl)-3-(4-{6-[(3-methoxy-propyl)-methyl-amino]-pyridin-3-yl}-naphthalen-1-yl)-urea;

1-(5-tert-Butyl-2-methyl-phenyl)-3-[4-(4-morpholin-4-ylmethyl-imidazol-1-yl)-naphthalen-1-yl]-urea;

1-(5-tert-Butyl-2-methyl-phenyl)-3-[4-(4-morpholin-4-ylmethyl-phenyl)-naphthalen-1-yl]-urea;

1-(5-tert-Butyl-2-methyl-phenyl)-3-[4-(6-morpholin-4-ylmethyl-pyridin-3-yl)-naphthalen-1-yl]-urea;

1-(5-tert-Butyl-2-methyl-phenyl)-3-{4-[6-(3-methoxy-propylamino)-pyridin-3-yl]-naphthalen-1-yl}-urea;

1-(5-tert-Butyl-2-methyl-pyridin-3-yl)-3-[4-(6-morpholin-4-ylmethyl-pyridin-3-yl)-naphthalen-1-yl]-urea;

1-(5-tert-Butyl-2-morpholin-4-yl-phenyl)-3-[4-(6-morpholin-4-ylmethyl-pyridin-3-yl)-naphthalen-1-yl]-urea;

1-(6-tert-Butyl-2-chloro-3-methyl-pyridin-4-yl)-3-[4-(6-morpholin-4-ylmethyl-pyridin-3-yl)-naphthalen-1-yl]-urea;

1-(6-tert-Butyl-2-chloro-3-methyl-pyridin-4-yl)-3-[4-(6-thiomorpholin-4-ylmethyl-pyridin-3-yl)-naphthalen-1-yl]-urea;

1-[2-Methoxy-5-(1-methyl-cyclopropyl)-phenyl]-3-[4-(2-morpholin-4-ylmethyl-pyrimidin-5-yl)-naphthalen-1-yl]-urea;

1-[4-(6-Morpholin-4-ylmethyl-pyridin-3-yl)-naphthalen-1-yl]-3-(3-trifluoromethyl-phenyl)-urea;

1-[4-(6-Morpholin-4-ylmethyl-pyridin-3-yl)-naphthalen-1-yl]-3-(4-trifluoromethoxy-phenyl)-urea;

1-[5-(1,1-Dimethyl-propyl)-2-methoxy-phenyl]-3-[4-(4-thiomorpholin-4-ylmethyl-phenyl)-naphthalen-1-yl]-urea;

1-[5-(1,1-Dimethyl-propyl)-2-methoxy-phenyl]-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(2-morpholin-4-ylmethyl-pyrimidin-5-yl)-naphthalen-1-yl]-urea;

1-[5-tert-Butyl-2-(1H-pyrazol-4-yl)-phenyl]-3-[4-(6-morpholin-4-ylmethyl-pyridin-3-yl)-naphthalen-1-yl]-urea;

1-[5-tert-Butyl-2-(2-methyl-pyrimidin-5-yl)-phenyl]-3-[4-(5-pyridin-4-ylmethyl-pyridin-2-yl)-naphthalen-1-yl]-urea;

1-[5-tert-Butyl-2-(2-methyl-pyrimidin-5-yl)-phenyl]-3-[4-(6-morpholin-4-ylmethyl-pyridin-3-yl)-naphthalen-1-yl]-urea;

1-[5-tert-Butyl-2-(3-hydroxy-propyl)-phenyl]-3-[4-(6-morpholin-4-ylmethyl-pyridin-3-yl)-naphthalen-1-yl]-urea;

1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea;

1-[5-tert-Butyl-2-(morpholine-4-carbonyl)-phenyl]-3-[4-(6-morpholin-4-ylmethyl-pyridin-3-yl)-naphthalen-1-yl]-urea;

2-[4-tert-Butyl-2-(3-{4-[6-(2,6-dimethyl-morpholin-4-ylm-ethyl)-pyridin-3-yl]-naphthalen-1-yl}-ureido)-phenoxy]-acetamide;

3-{4-[3-(5-tert-Butyl-2-methoxy-phenyl)-ureido]-naphthalen-1-yl}-benzamide;

4-tert-Butyl-2-{3-[4-(2-chloro-4-morpholin-4-ylmethyl-phenyl)-naphthalen-1-yl]-ureido}-benzamide;

and the pharmaceutically acceptable derivatives thereof.

In another embodiment of the invention there are provided the following compounds of formula(II) which are useful in the novel methods described herein:

1-(2-tert-Butyl-5-methyl-pyridin-4-yl)-3-[4-(6-morpholin-4-ylmethyl-pyridin-3-yl)-naphthalen-1-yl]-urea;

1-(3-tert-Butyl-phenyl)-3-[4-(6-morpholin-4-ylmethyl-pyridin-3-yl)-naphthalen-1-yl]-urea;

1-(4-Methyl-biphenyl-3-yl)-3-[4-(6-morpholin-4-ylmethyl-pyridin-3-yl)-naphthalen-1-yl]-urea;

1-(4-tert-Butyl-biphenyl-2-yl)-3-[4-(6-morpholin-4-ylm-ethyl-pyridin-3-yl)-naphthalen-1-yl]-urea;

1-(5-Isopropyl-2-methyl-phenyl)-3-[4-(6-morpholin-4-ylm-ethyl-pyridin-3-yl)-naphthalen-1-yl]-urea;

1-(5-sec-Butyl-2-methoxy-phenyl)-3-[4-(6-morpholin-4-ylmethyl-pyridin-3-yl)-naphthalen-1-yl]-urea;

1-(5-tert-Butyl-2-methoxymethyl-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-morpholin-4-ylmethyl-pyridin-3-yl)-naphthalen-1-yl]-urea;

1-(5-tert-Butyl-2-methyl-phenyl)-3-(4-{6-[(3-methoxy-propyl)-methyl-amino]-pyridin-3-yl}-naphthalen-1-yl)-urea;

1-(5-tert-Butyl-2-methyl-phenyl)-3-[4-(6-morpholin-4-ylm-ethyl-pyridin-3-yl)-naphthalen-1-yl]-urea;

1-(5-tert-Butyl-2-methyl-pyridin-3-yl)-3-[4-(6-morpholin-4-ylmethyl-pyridin-3-yl)-naphthalen-1-yl]-urea;

1-[5-(1,1-Dimethyl-propyl)-2-methoxy-phenyl]-3-[4-(6-morpholin-4-ylmethyl-pyridin-3-yl)-naphthalen-1-yl]-urea;

1-[5-tert-Butyl-2-(1H-pyrazol-4-yl)-phenyl]-3-[4-(6-morpholin-4-ylmethyl-pyridin-3-yl)-naphthalen-1-yl]-urea;

1-[5-tert-Butyl-2-(2-methyl-pyrimidin-5-yl)-phenyl]-3-[4-(6-morpholin-4-ylmethyl-pyridin-3-yl)-naphthalen-1-y]-urea;

1-[5-tert-Butyl-2-(3-hydroxy-propyl)-phenyl]-3-[4-(6-morpholin-4-ylmethyl-pyridin-3-yl)-naphthalen-1-yl]-urea;

1-[5-tert-Butyl-2-(morpholine-4-carbonyl)-phenyl]-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylm-ethyl-pyridin-3-yl)-naphthalen-1-yl]-ureido}-phenyl)-acetamide and the pharmaceutically acceptable derivatives thereof.

In a fourth broad generic aspect, there is provided a method of treating a cytokine mediated disease or condition chosen from: acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure, said method comprising administering to a patient in need of such treatment a therapeutically effective amount of a compound of the formula (III) disclosed in WO 00/55139 which is the PCT case of U.S. application Ser. No. 09/505,582:

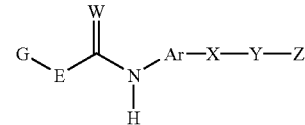

(III)

wherein:

E is carbon or a heteroatom group chosen from —O—, —NH— and —S—;

G is:

an aromatic $C_{6-10}$ carbocycle or a nonaromatic $C_{3-10}$ carbocycle saturated or unsaturated;

a 6–14 membered monocyclic, bicyclic or tricyclic heteroaryl containing 1 or more heteroatoms chosen from O, N and S;

a 6–8 membered monocyclic heterocycle containing one or more heteroatoms chosen from O, N and S;

or an 8–11 membered bicyclic heterocycle, containing one or more heteroatoms chosen from O, N and S;

wherein G is optionally substituted by one or more $R_1$, $R_2$ or $R_3$;

Ar is:

phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:

a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;

aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated or unsaturated branched or unbranched carbon chain optionally partially or fully halogenated, wherein one or more C atoms are optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is:

aryl, heteroaryl selected from pyridinyl, piperazinyl, pyrimidinyl, pyridazinyl, pyrazinyl, imidazolyl, pyrazolyl, triazolyl, tetrazolyl, furanyl, thienyl and pyranyl, heterocycle selected from tetrahydropyrimidonyl, cyclohexanonyl, cyclohexanolyl, 2-oxa- or 2-thia-5-aza-bicyclo [2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, halogen, nitrile, amino wherein the N atom is optionally independently mono- or di-substituted by $C_{1-3}$acyl, $C_{1-6}$alkyl or $C_{1-3}$alkoxy$C_{1-3}$alkyl, $C_{1-6}$alkyl branched or unbranched, $C_{1-6}$alkoxy, $C_{1-3}$acylamino, nitrile$C_{1-4}$alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:

$C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl, pyridinyl, pyrimidinyl, pyrazinyl, pyridazinyl, pyrrolyl, pyrrolidinyl, imidazolyl, pyrazolyl, thienyl, furyl, dioxolanyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl)amino, and mono- or di($C_{1-3}$alkyl) aminocarbonyl;

or $R_1$ is cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloalkyl group wherein one to three ring methylene groups are independently replaced by O, $S(O)_m$, CHOH, >C=O, >C=S or NH;

phenyloxy or benzyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloaryl group wherein one to two ring methyne groups are independently replaced by N;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three $C_{1-3}$ alkyl optionally partially or fully halogenated, nitrile, hydroxy$C_{1-3}$ alkyl or aryl; or an analog of such cycloalkyl group wherein one to three ring methylene groups are independently replaced by O, $S(O)_m$, CHOH, >C=O, >C=S or NH;

$C_{3-10}$ branched or unbranced alkenyl each being optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with one to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di($C_{1-3}$alkyl)aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

oxo, nitrile, halogen;

silyl containing three $C_{1-4}$ alkyl groups optionally partially or fully halogenated; or $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, halogen, methoxycarbonyl, $C_{1-3}$ alkyl-$S(O)_m$ optionally partially or fully halogenated, or phenyl-$S(O)_m$;

$OR_6$, $C_{1-6}$ alkoxy, hydroxy, nitrile, nitro, halogen;

or amino-$S(O)_m$— wherein the N atom is optionally independently mono- or di-substituted by $C_{1-6}$alkyl or aryl$C_{0-3}$ alkyl, or amino wherein the N atom is optionally independently mono- or di-substituted by $C_{1-3}$alkyl, aryl$C_{0-3}$alkyl, $C_{1-6}$acyl, $C_{1-6}$alkyl-$S(O)_m$— or aryl$C_{0-3}$ alkyl-$S(O)_m$—, each of the aforementioned alkyl and aryl in this subparagraph are optionally partially or fully halogenated and optionally substituted with one to two $C_{1-6}$ alkyl or $C_{1-6}$alkoxy;

each $R_3$ is independently:

phenyl, naphthyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—$C(O)$—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally be partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-$S(O)_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$—, $R_{23}R_{24}NC(O)$—$C_{1-3}$alkoxy or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, $S(O)_m$ and wherein said alkynyl group is optionally independently substituted with one to two oxo groups, pyrroldinyl, pyrrolyl, morpholino, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$alkyl)amino optionally substituted by one or more halogen atoms;

$C_{1-6}$acyl or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently:

nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}$, $R_{23}$ and $R_{24}$ is independently:

hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino;

or $R_{23}$ and $R_{24}$ taken together optionally form a heterocyclic or heteroaryl ring;

m=0, 1 or 2;

W is O or S and the pharmaceutically acceptable derivatives thereof.

A preferred subgeneric aspect of the invention comprises a method of using the compounds of the formula(III) as provided above and wherein:

E is —$CH_2$—, —NH— or —O—;

W is O;

and

G is:

phenyl, naphthyl, benzocyclobutanyl, dihydronaphthyl, tetrahydronaphthyl, benzocycloheptanyl, benzocycloheptenyl, indanyl, indenyl;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, 2,3-dihydro-1H-indolyl, indolinyl, indolonyl, indolinonyl, phthalimidyl, chromoyl;

oxetanyl, pyrrolidinyl, tetrahydrofuranyl, tetrahydrothiophenyl, piperidinyl, piperazinyl, morpholino, tetrahydropyranyl, dioxanyl, tetramethylene sulfonyl, tetramethylene sulfoxidyl, oxazolinyl, 3,4-dihydro-2H-benzo[1,4]oxazinyl, thiazolinyl, imidazolinyl, tertrahydropyridinyl, homopiperidinyl, pyrrolinyl, tetrahydropyrimidinyl, decahydroisoquinolinyl, decahydroquinolinyl, thiomorpholino, thiazolidinyl, dihydrooxazinyl, dihydropyranyl, oxocanyl, heptacanyl, thioxanyl or dithianyl; wherein G is optionally substituted by one or more $R_1$, $R_2$ or $R_3$.

A more preferred subgeneric aspect of the invention comprises a method of using the compounds of the formula (III) as provided above and wherein:

E is —NH—;

G is phenyl, pyridinyl, pyridonyl, naphthyl, quinolinyl, isoquinolinyl, pyrazinyl, benzimidazolyl, benzooxazolyl, benzooxazolonyl, benzofuranyl, benzothiophenyl, benzpyrazolyl, dihydrobenzofuranyl, dihydrobenzothiophenyl, 3,4-dihydro-2H-benzo[1,4]oxazinyl, indanyl, indenyl, indolyl, indolinyl, indolonyl, 2,3-dihydro-1H-indolyl or indolinonyl, wherein G is optionally substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated or unsaturated carbon chain wherein one or more of the C atoms is optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is:

phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-azabicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

or Z is optionally substituted by phenyl, heterocycle or heteroaryl as hereinabove described in this paragraph each in turn is optionally substituted by halogen, $C_{1-3}$ alkyl or $C_{1-3}$ alkoxy;

or Z is nitrile, nitrile$C_{1-3}$ alkyl, $C_{1-6}$ alkyl-$S(O)_m$, halogen, hydroxy, $C_{1-3}$ alkyl, $C_{1-3}$ acylamino, $C_{1-4}$ alkoxy, amino, mono- or di-($C_{1-3}$ alkyl)aminocarbonyl, or amino mono or di-substituted by amino$C_{1-6}$ alkyl or $C_{1-3}$alkoxy$C_{1-3}$alkyl;

each $R_1$ is independently:

$C_{1-6}$ alkyl branched or unbranched optionally partially or fully halogenated, wherein one or more C atoms are optionally independently replaced by O, N or $S(O)_m$, and wherein said $C_{1-6}$ alkyl is optionally substituted with one to three $C_{3-6}$cycloalkyl, oxo, phenyl, dioxolanyl, pyrrolidinyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile and $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; or an analog of such cycloalkyl group wherein one to three ring methylene groups are independently replaced by O, S, CHOH, >C=O, >C=S or NH;

oxo;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

or silyl containing three $C_{1-4}$ alkyl groups optionally partially or fully halogenated;

$R_2$ is independently:

a $C_{1-5}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-2}$ alkyl-$S(O)_m$ optionally partially or fully halogenated, or phenyl-$S(O)_m$;

$C_{1-3}$ alkoxy, hydroxy, nitrile, nitro, halogen;

or amino-$S(O)_m$— wherein the N atom is optionally independently mono- or di-substituted by $C_{1-3}$alkyl or aryl$C_{0-3}$ alkyl, or amino wherein the N atom is optionally independently mono- or di-substituted by $C_{1-3}$alkyl, aryl$C_{0-3}$alkyl, $C_{1-3}$acyl, $C_{1-4}$alkyl-$S(O)_m$— or aryl$C_{0-3}$alkyl-$S(O)_m$—, each of the aforementioned alkyl and aryl in this subparagraph are optionally partially or fully halogenated and optionally substituted with one to two $C_{1-3}$ alkyl or $C_{1-3}$ alkoxy;

$R_3$ is independently:

phenyl, morpholino, pyridinyl, pyrimidinyl, pyrazinyl, pyrrolyl, pyrrolidinyl, imidazolyl, [1,3,4]oxadiazol, pyrazolyl, each is optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkoxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl)aminocarbonyl, $C_{1-5}$ alkyl-$C(O)$—$C_{1-4}$ alkyl, mono- or di-($C_{1-3}$alkyl)amino, mono- or di-($C_{1-3}$) alkylamino-$C_{1-5}$ alkyl, mono- or di-($C_{1-3}$alkyl)amino-S$(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl($R_{11}$)N, carboxy-mono- or di-($C_{1-5}$)-alkyl-amino;

$C_{1-3}$ alkyl or $C_{1-4}$ alkoxy each being optionally partially or fully halogenated or optionally substituted with $R_{17}$;

$OR_{18}$ or $C_{1-6}$ alkyl optionally substituted with $OR_{18}$;

amino or mono- or di-($C_{1-5}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$—, $R_{23}R_{24}NC(O)$—$C_{1-2}$alkoxy or $R_{26}C(O)CH_2N(R_{21})$—;

$C_{2-4}$alkenyl substituted by $R_{23}R_{24}NC(O)$—; or $C_{2-4}$ alkynyl branched or unbranched carbon chain optionally partially or fully halogenated wherein one of the methylene groups is optionally replaced by O, and optionally independently substituted with one to two oxo groups, pyrroldinyl, pyrrolyl, morpholino, piperidinyl, piperazinyl, imidazolyl, phenyl, pyridinyl, tetrazolyl or one or more $C_{1-4}$ alkyl optionally substituted by one or more halogen atoms;

$C_{1-3}$acyl; and $R_{23}$ and $R_{24}$ taken together optionally form imidazolyl, piperidinyl, morpholino, piperazinyl or a pyridinyl ring.

A yet more preferred subgeneric aspect of the invention comprises a method of using the compounds of the formula (III), as described in the immediate previous paragraph, wherein:

G is phenyl, pyridinyl, pyridonyl, naphthyl, quinolinyl, isoquinolinyl, pyrazinyl, 3,4-dihydro-2H-benzo[1,4]oxazinyl, benzothiophenyl, dihydrobenzofuranyl, dihydrobenzothiophenyl, benzooxazolyl, indanyl, indolyl, indolinyl, indolonyl or indolinonyl, wherein G is optionally substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated carbon chain wherein one or more of the C atoms is optionally replaced by O, N or S and wherein Y is optionally independently substituted with nitrile or oxo;

Z is:

phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo [2.2.1]heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy; or Z is hydroxy, $C_{1-3}$ alkyl, $C_{1-3}$ alkoxy, $C_{1-3}$ acylamino, $C_{1-3}$ alkylsulfonyl, nitrile $C_{1-3}$ alkyl or amino mono or di-substituted by $C_{1-3}$ alkoxy$C_{1-3}$ alkyl;

each $R_1$ is independently:

$C_{1-5}$ alkyl branched or unbranched optionally partially or fully halogenated, wherein one or more C atoms are optionally independently replaced by O, N or $S(O)_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O;

oxo;

$C_{2-4}$ alkynyl optionally partially or fully halogenated wherein one or more methylene groups are optionally replaced by O, and optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

or silyl containing three $C_{1-2}$ alkyl groups optionally partially or fully halogenated;

each $R_2$ is independently:

a $C_{1-4}$ alkyl optionally partially or fully halogenated, $C_{1-4}$ alkoxy optionally partially or fully halogenated, bromo, chloro, fluoro, methoxycarbonyl, methyl-$S(O)_m$, ethyl-$S(O)_m$ each optionally partially or fully halogenated or phenyl-$S(O)_m$;

or $R_2$ is mono- or di-$C_{1-3}$acylamino, amino-$S(O)_m$ or $S(O)_m$ amino wherein the N atom is mono- or di-substituted by $C_{1-3}$alkyl or phenyl, nitrile, nitro or amino;

each $R_3$ is independently:

phenyl, morpholino, pyridinyl, pyrimidinyl, pyrrolidinyl, 2,5-pyrrolidin-dionyl, imidazolyl, [1,3,4]oxadiazol, pyrazolyl, each of the aforementioned is optionally substituted with one to three $C_{1-3}$ alkyl which is optionally partially or fully halogenated, halogen, oxo, hydroxy, nitrile and $C_{1-3}$ alkoxy optionally partially or fully halogenated;

$C_{1-3}$ alkyl or $C_{1-3}$ alkoxy optionally partially or fully halogenated or optionally substituted with $R_{17}$;

$OR_{18}$ or $C_{1-3}$ alkyl optionally substituted with $OR_{18}$;

amino or mono- or di-($C_{1-3}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl;

$C_{1-3}$acyl and $R_{23}$ and $R_{24}$ taken together optionally form morpholino.

A yet further preferred subgeneric aspect of the invention comprises a method of using the compounds of the formula (III), as described in the immediate previous paragraph, and wherein:

G is phenyl, pyridinyl, pyridonyl, 2-naphthyl, quinolinyl, isoquinolinyl, dihydrobenzofuranyl, indanyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl, indolinyl, indolonyl, or indolinonyl, wherein G is optionally substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or

—$CH_2$—, —$CH_2CH_2$—, —$C(O)$—, —$O$—, —$S$—, —$NH$—$CH_2CH_2CH_2$—, —$N(CH_3)$—, $CH_2(CN)CH_2$—NH—$CH_2$ or —NH—;

Z is morpholino, dioxolanyl, tetrahydrofuranyl, pyridinyl, 2-oxa-5-aza-bicyclo[2.2.1]heptanyl, $C_{1-3}$alkoxyphenylpiperazinyl, hydroxy, $C_{1-3}$alkyl, N,N-di$C_{1-3}$alkoxy$C_{1-3}$ alkylamino, $C_{1-3}$acylamino, $C_{1-3}$alkylsulfonyl or nitrile$C_{1-3}$alkyl;

each $R_1$ is independently:

$C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$alkoxy;

cyclopropyl, cyclopentanyl, cyclohexanyl and bicyclopentanyl optionally substituted with one to three methyl groups optionally partially or fully halogenated, nitrile, hydroxymethyl or phenyl; or 2-tetrahydrofuranyl substituted by methyl; or trimethyl silyl;

propynyl substituted hydroxy or tetrahydropyran-2-yloxy;

$R_2$ is is mono- or di-$C_{1-3}$acylamino, amino-$S(O)_m$ or $S(O)_m$ amino wherein the N atom is mono- or di-substituted by $C_{1-3}$alkyl or phenyl, bromo, chloro, fluoro, nitrile, nitro, amino, methylsulfonyl optionally partially or fully halogenated or phenylsulfonyl;

each $R_3$ is independently:

phenyl, morpholino, pyridinyl, pyrimidinyl, pyrrolidinyl, 2,5-pyrrolidin-dionyl, imidazolyl, [1,3,4]oxadiazol or pyrazolyl, each is optionally substituted with $C_{1-2}$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;

$C_{2-4}$alkenyl substituted by $R_{23}R_{24}NC(O)$—; or $C_{2-4}$ alkynyl substituted with pyrroldinyl or pyrrolyl;

$C_{1-2}$acyl; and $R_{23}$ and $R_{24}$ are H or $R_{23}$ and $R_{24}$ taken together optionally form morpholino; and $R_{26}$ is morpholino.

A further preferred subgeneric aspect of the invention comprises a method of using the compounds of the formula (III), as described in the immediate previous paragraph, and wherein:

G is phenyl, pyridinyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl or 2-naphthyl wherein G is optionally substituted by one or more $R_1$, $R_2$ or $R_3$;

X is:

imidazolyl, pyridinyl, pyrimidinyl or pyrazinyl;

Y is:

a bond, $CH_2(CN)CH_2$—NH—$CH_2$, —$CH_2$—, —NH—$CH_2CH_2CH_2$— or —NH—;

Z is morpholin-4yl, dioxolan-2yl, tetrahydrofuranyl, pyridinyl, 2-oxa-5-aza-bicyclo[2.2.1]hept-5yl, methoxyphenylpiperazinyl, hydroxy, methyl, N,N-dimethoxyethylamino, acetylamino, methylsulfonyl or cyanoethyl;

each $R_1$ is independently:

tert-butyl, sec-butyl, tert-amyl, phenyl, tetrahydropyran-2-yloxypropynyl, hydroxypropynyl, trihalomethyl, 2,2-diethylpropionyl or cyclohexanyl;

$R_2$ is chloro, nitro, amino, nitrile, methylsulfonylamino, diacetylamino, phenylsulfonylamino, N,N-di(methylsulfonyl)amino, methylsulfonyl or trihalomethylsulfonyl;

$R_3$ is independently:

methyl, $C_{1-3}$ alkoxy, methoxymethyl, hydroxypropyl, dimethylamino, $C_{1-4}$alkylamino, $NH_2C(O)$methoxy, acetyl, pyrrolidinyl, imidazolyl, pyrazolyl, morpholino or morpholinocarbonyl.

A still yet further preferred subgeneric aspect of the invention comprises a method of using the compounds of the formula (III), as described in the immediate previous paragraph, and wherein:

X is pyridinyl.

A still yet further preferred subgeneric aspect of the invention comprises a method of using the compounds of the formula (III), as described immediately above, and wherein the pyridinyl is attached to Ar via the 3-pyridinyl position.

The following compounds are representative of the compounds of formula(II) which are useful in the novel methods described herein:

1-(4-tert-Butyl-phenyl)-3-[4-(6-morpholin-4-ylmethyl-pyridin-3-yl)-naphthalen-1-yl]-urea;

1-(5-tert-Butyl-2-methyl-phenyl)-3-[4-(4-morpholin-4-ylmethyl-piperidin-1-yl)-naphthalen-1-yl]-urea;

1-(6-Chloro-4-trifluoromethyl-pyridin-2-yl)-3-[4-(6-morpholin-4-ylmethyl-pyridin-3-yl)-naphthalen-1-yl]-urea;

1-(4-Difluoromethoxy-phenyl)-3-[4-(6-morpholin-4-ylmethyl-pyridin-3-yl)-naphthalen-1-yl]-urea;

1-(3-Methyl-naphthalen-2-yl)-3-[4-(6-morpholin-4-ylmethyl-pyridin-3-yl)-naphthalen-1-yl]-urea;

1-[2-Methoxy-5-(1-methyl-1-phenyl-ethyl)-phenyl]-3-[4-(6-morpholin-4-ylmethyl-pyridin-3-yl)-naphthalen-1-yl]-urea;

(5-tert-Butyl-2-methyl-phenyl)-carbamic acid 3-(5-{4-[3-(5-tert-butyl-2-methyl-phenyl)-ureido]-naphthalen-1-yl}-pyridin-2-ylamino)-propyl ester;

1-(6-tert-Butyl-benzo[1,3]dioxol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1,3-Bis-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-hydroxy-phenyl]-3-[4-(6-morpholin-4-ylmethyl-pyridin-3-yl)-naphthalen-1-yl]-urea;

1-[5-tert-Butyl-2-(2-pyrrolidin-1-yl-ethoxy)-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(2-p-tolyloxy-5-trifluoromethyl-phenyl)-urea;

1-[2-(2-Methoxy-phenoxy)-5-trifluoromethyl-phenyl]-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-naphthalen-1-yl-urea;

1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-{5-tert-Butyl-2-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-(5-Hydroxymethyl-2-methyl-phenyl)-3-[4-(6-morpholin-4-ylmethyl-pyridin-3-yl)-naphthalen-1-yl]-urea;

1-(2-Methoxy-dibenzofuran-3-yl)-3-[4-(6-morpholin-4-ylmethyl-pyridin-3-yl)-naphthalen-1-yl]-urea;

1-(2,5-Di-tert-butyl-phenyl)-3-[4-(6-morpholin-4-ylmethyl-pyridin-3-yl)-naphthalen-1-yl]-urea;

1-[3-(4-Bromo-1-methyl-1H-pyrazol-3-yl)-phenyl]-3-[4-(6-morpholin-4-ylmethyl-pyridin-3-yl)-naphthalen-1-yl]-urea;

1-(3-Hydroxy-5,6,7,8-tetrahydro-naphthalen-2-yl)-3-[4-(6-morpholin-4-ylmethyl-pyridin-3-yl)-naphthalen-1-yl]-urea;

1-(1-Acetyl-2,3-dihydro-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-oxazol-5-yl-phenyl)-urea;

1-[4-(6-Morpholin-4-ylmethyl-pyridin-3-yl)-naphthalen-1-yl]-3-(3-[1,3,4]oxadiazol-2-yl-phenyl)-urea;

1-(2-Methoxy-5-trifluoromethyl-phenyl)-3-[4-(6-morpholin-4-ylmethyl-pyridin-3-yl)-naphthalen-1-yl]-urea;

Furan-2-carboxylic acid (4-tert-butyl-2-{3-[4-(6-morpholin-4-ylmethyl-pyridin-3-yl)-naphthalen-1-yl]-ureido}-phenyl)-amide;

1-(2-Methoxy-4-phenylamino-phenyl)-3-[4-(6-morpholin-4-ylmethyl-pyridin-3-yl)-naphthalen-1-yl]-urea;

1-(5-Methoxy-2-methyl-phenyl)-3-[4-(6-morpholin-4-ylmethyl-pyridin-3-yl)-naphthalen-1-yl]-urea;

1-(3-Hydroxy-naphthalen-2-yl)-3-[4-(6-morpholin-4-ylmethyl-pyridin-3-yl)-naphthalen-1-yl]-urea;

N,N-Diethyl-4-methoxy-3-{3-[4-(6-morpholin-4-ylmethyl-pyridin-3-yl)-naphthalen-1-yl]-ureido}-benzenesulfonamide;

1-(2,2-Difluoro-benzo[1,3]dioxol-5-yl)-3-[4-(6-morpholin-4-ylmethyl-pyridin-3-yl)-naphthalen-1-yl]-urea;

1-[5-(1,1-Dimethyl-propyl)-2-phenoxy-phenyl]-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]-urea;

2-Chloro-5-{3-[4-(6-morpholin-4-ylmethyl-pyridin-3-yl)-naphthalen-1-yl]-ureido}-benzoic acid isopropyl ester;

1-(4-Amino-3,5-dibromo-phenyl)-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

2-(5-tert-Butyl-2-methoxy-phenyl)-N-[4-(6-morpholin-4-ylmethyl-pyridin-3-yl)-naphthalen-1-yl]-acetamide;

1-(2-Methoxy-5-phenoxy-phenyl)-3-[4-(6-morpholin-4-ylmethyl-pyridin-3-yl)-naphthalen-1-yl]-urea;

1-(3,3-Dimethyl-2-oxo-2,3-dihydro-1H-indol-7-yl)-3-[4-(6-morpholin-4-ylmethyl-pyridin-3-yl)-naphthalen-1-yl]-urea;

1-(5-tert-Butyl-2-cyclopentyloxy-phenyl)-3-[4-(6-morpholin-4-ylmethyl-pyridin-3-yl)-naphthalen-1-yl]-urea;

1-(5-tert-Butyl-2-methoxy-phenyl)-3-{4-[6-(3-pyridin-3-yl-pyrrolidin-1-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(6-tert-Butyl-3-oxo-3,4-dihydro-2H-benzo[1,4]oxazin-7-yl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-[6-tert-Butyl-4-(2-morpholin-4-yl-ethyl)-3-oxo-3,4-dihydro-2H-benzo[1,4]oxazin-8-yl]-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

N-(5-tert-Butyl-2-methoxy-4-{3-[4-(6-morpholin-4-ylmethyl-pyridin-3-yl)-naphthalen-1-yl]-ureido}-phenyl)-methanesulfonamide;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-(2-Ethanesulfonyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(3-dimethylamino-pyrrolidin-1-ylmethyl)-pyridin-3-yl]-naphthalen-1-yl}-urea;

N-[1-(5-{4-[3-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-{3-[4-(6-morpholin-4-ylmethyl-pyridin-3-yl)-naphthalen-1-yl]-ureido}-phenyl)-isobutyramide;

2-(4-tert-Butyl-2-{3-[4-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(6-tert-Butyl-3-cyano-2-methoxymethoxy-pyridin-4-yl)-3-[4-(6-morpholin-4-ylmethyl-pyridin-3-yl)-naphthalen-1-yl]-urea;

1-(6-tert-Butyl-3-cyano-2-hydroxy-pyridin-4-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(1,3,3-trimethyl-2,3-dihydro-1H-indol-5-yl)-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(4-morpholin-4-ylmethyl-piperidin-1-yl)-naphthalen-1-yl]-urea;

1-[5-tert-Butyl-2-(1-methyl-1H-pyrazol-4-yl)-phenyl]-3-[4-(4-morpholin-4-ylmethyl-piperidin-1-yl)-naphthalen-1-yl]-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-3-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

N-(5-{4-[3-(5-tert-Butyl-2-methyl-phenyl)-ureido]-naphthalen-1-yl}-pyrazin-2-yl)-methanesulfonamide;

1-[4-(6-{[Bis-(2-cyano-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;

1-(5-tert-Butyl-2-methoxy-phenyl)-3-{4-[6-(2-methoxyethyl-morpholin-4-ylmethyl)-pyridin-3-yl]-naphthalen-1-yl}-urea;

1-(5-tert-Butyl-2-methoxy-phenyl)-3-(4-{6-[(2-morpholin-4-yl-ethylamino)-methyl]-pyridin-3-yl}-naphthalen-1-yl)-urea;

1-(5-tert-Butyl-2-methoxy-phenyl)-3-{4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-{4-[3-(5-tert-Butyl-2-methoxy-phenyl)-ureido]-naphthalen-1-yl}-pyridin-2-ylmethyl)-piperidine-4-carboxylic acid amide;

1-(5-tert-Butyl-2-methoxy-phenyl)-3-{4-[6-(1-oxo-1l4-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-{4-[6-(4-Acetyl-piperazin-1-ylmethyl)-pyridin-3-yl]-naphthalen-1-yl}-3-(5-tert-butyl-2-methoxy-phenyl)-urea;

4-(5-{4-[3-(5-tert-Butyl-2-methoxy-phenyl)-ureido]-naphthalen-1-yl}-pyridin-2-ylmethyl)-piperazine-1-carboxylic acid ethyl ester;

1-(5-tert-Butyl-2-methoxy-phenyl)-3-(4-{6-[(2-pyridin-3-yl-ethylamino)-methyl]-pyridin-3-yl}-naphthalen-1-yl)-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-(4-{6-[(2-methylsulfanyl-ethylamino)-methyl]-pyridin-3-yl}-naphthalen-1-yl)-urea;

1-(5-tert-Butyl-2-methoxy-phenyl)-3-{4-[6-(2-oxa-5-azabicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]naphthalen-1-yl}-urea;

1-(5-tert-Butyl-2-methoxy-phenyl)-3-(4-{6-[(2-piperazin-1-yl-ethylamino)-methyl]-pyridin-3-yl}-naphthalen-1-yl)-urea;

1-(5-tert-Butyl-2-methoxy-phenyl)-3-{4-[6-(4-pyrimidin-2-yl-piperazin-1-ylmethyl)-pyridin-3-yl]-naphthalen-1-yl}-urea;

1-(5-tert-Butyl-2-methoxy-phenyl)-3-{4-[6-(4-pyridin-2-yl-piperazin-1-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-{4-[6-(2-thia-5-azabicyclo[2.2.1]hept-5-ylmethyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

1-(5-tert-Butyl-2-methoxy-phenyl)-3-{4-[6-(pyridin-3-ylamino)-pyridin-3-yl]-naphthalen-1-yl}-urea;

[4-(6-Morpholin-4-ylmethyl-pyridin-3-yl)-naphthalen-1-yl]-carbamic acid 3-tert-butyl-phenyl ester;

N-(5-tert-Butyl-2-methoxy-3-{3-[4-(6-morpholin-4-ylmethyl-pyridin-3-yl)-naphthalen-1-yl]-ureido}-phenyl)-methanesulfonamide and the pharmaceutically acceptable derivatives thereof.

In another embodiment of the invention there are provided the following compounds of formula(III) which are useful in the novel methods described herein:

1-(3-Methyl-naphthalen-2-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-(2-Methoxy-5-trifluoromethyl-phenyl)-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;
1-(5-tert-Butyl-2-imidazol-1-yl-phenyl)-3-[4-(6-morpholin-4-ylmethyl-pyridin-3-yl)-naphthalen-1-yl]-urea;
1-(5-tert-Butyl-3-ethylamino-2-methoxy-phenyl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;
1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;
1-(2-Methanesulfinyl-5-trifluoromethyl-phenyl)-3-[4-(6-morpholin-4-ylmethyl-pyridin-3-yl)-naphthalen-1-yl]-urea;
1-[4-(6-{[Bis-(2-methoxy-ethyl)-amino]-methyl}-pyridin-3-yl)-naphthalen-1-yl]-3-(5-tert-butyl-2-methoxy-phenyl)-urea;
N-[1-(5-{4-[3-(5-tert-Butyl-2-methoxy-phenyl)-ureido]-naphthalen-1-yl}-pyridin-2-ylmethyl)-pyrrolidin-3-yl]-acetamide;
1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-propionamide;
1-(5-tert-Butyl-2-methyl-benzooxazol-7-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3-trifluoromethanesulfonyl-phenyl)-urea;
N-(5-tert-Butyl-2-methoxy-3-{3-[4-(6-morpholin-4-ylmethyl-pyridin-3-yl)-naphthalen-1-yl]-ureido}-phenyl)-isobutyramide;
2-(4-tert-Butyl-2-{3-[4-(6-morpholin-4-ylmethyl-pyridin-3-yl)-naphthalen-1-yl]-ureido}-phenoxy)-acetamide;
1-(5-tert-Butyl-2-oxo-2,3-dihydro-benzooxazol-7-yl)-3-[4-(6-morpholin-4-ylmethyl-pyridin-3-yl)-naphthalen-1-yl]-urea;
1-(5-tert-Butyl-3-cyano-2-methoxy-phenyl)-3-[4-(6-morpholin-4-ylmethyl-pyridin-3-yl)-naphthalen-1-yl]-urea;
1-(5-tert-Butyl-benzooxazol-7-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-benzenesulfonamide;
Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
1-(5-tert-Butyl-2-methoxy-phenyl)-3-[4-(2-morpholin-4-ylmethyl-pyrimidin-5-yl)-naphthalen-1-yl]-urea;
1-(5-tert-Butyl-2-methylsulfanyl-phenyl)-3-[4-(6-morpholin-4-ylmethyl-pyridin-3-yl)-naphthalen-1-yl]-urea;
1-(5-tert-Butyl-2-methoxy-pyridin-3-yl)-3-[4-(6-morpholin-4-ylmethyl-pyridin-3-yl)-naphthalen-1-yl]-urea;
2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
N-(5-{4-[3-(5-tert-Butyl-2-methyl-phenyl)-ureido]-naphthalen-1-yl}-pyrazin-2-yl)-methanesulfonamide;
1-[4-(6-{[Bis-(2-cyano-ethyl)-amino]-methyl}-pyridin-3-yl)-naphthalen-1-yl]-3-(5-tert-butyl-2-methoxy-phenyl)-urea;
1-(5-tert-Butyl-2-methoxy-phenyl)-3-{4-[6-(4-methyl-piperazin-1-ylmethyl)-pyridin-3-yl]-naphthalen-1-yl}-urea;
1-(5-tert-Butyl-2-methoxy-phenyl)-3-[4-(6-thiomorpholin-4-ylmethyl-pyridin-3-yl)-naphthalen-1-yl]-urea;
1-(5-tert-Butyl-2-methoxy-phenyl)-3-{4-[6-(2,6-dimethyl-piperidin-1-ylmethyl)-pyridin-3-yl]-naphthalen-1-yl}-urea;
1-(5-tert-Butyl-2-methoxy-phenyl)-3-{4-[6-(1-oxo-tetrahydro-thiopyran-4-ylamino)-pyridin-3-yl]-naphthalen-1-yl}-urea;
1-(5-tert-Butyl-2-methoxy-phenyl)-3-{4-[6-(tetrahydro-pyran-4-ylamino)-pyridin-3-yl]-naphthalen-1-yl}-urea;
1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;
1-(5-tert-Butyl-2-methoxy-phenyl)-3-{4-[6-(2-methoxymethyl-morpholin-4-ylmethyl)-pyridin-3-yl]-naphthalen-1-yl}-urea;
1-(5-tert-Butyl-2-methoxy-phenyl)-3-{4-[6-(2-methyl-3-oxo-piperazin-1-ylmethyl)-pyridin-3-yl]-naphthalen-1-yl}-urea;
1-(5-{4-[3-(5-tert-Butyl-2-methoxy-phenyl)-ureido]-naphthalen-1-yl}-pyridin-2-ylmethyl)-piperidine-3-carboxylic acid amide;
1-(5-tert-Butyl-2-methoxy-phenyl)-3-{4-[6-(1-oxo-1l4-thiomorpholin-4-ylmethyl)-pyridin-3-yl]-naphthalen-1-yl}-urea;
1-(3,3-Dimethyl-2-oxo-2,3-dihydro-1H-indol-5-yl)-3-[4-(6-morpholin-4-ylmethyl-pyridin-3-yl)-naphthalen-1-yl]-urea;
1-(5-tert-Butyl-2-methoxy-phenyl)-3-{4-[6-(3-oxo-piperazin-1-ylmethyl)-pyridin-3-yl]-naphthalen-1-yl}-urea;
1-(5-tert-Butyl-2-methoxy-phenyl)-3-(4-{6-[(tetrahydro-furan-3-ylamino)-methyl]-pyridin-3-yl}-naphthalen-1-yl)-urea;
1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;
1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;
1-(5-tert-Butyl-2-methoxy-phenyl)-3-{4-[6-(2,6-dimethyl-morpholin-4-ylmethyl)-pyridin-3-yl]-naphthalen-1-yl}-urea;
1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;
1-(5-tert-Butyl-2-methoxy-phenyl)-3-{4-[6-(morpholine-4-carbonyl)-pyridin-3-yl]-naphthalen-1-yl}-urea;
1-(5-tert-Butyl-2-methoxy-phenyl)-3-[4-(5-morpholin-4-ylmethyl-pyrazin-2-yl)-naphthalen-1-yl]-urea;
1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;
1-(3-Amino-5-tert-butyl-2-methoxy-phenyl)-3-[4-(6-morpholin-4-ylmethyl-pyridin-3-yl)-naphthalen-1-yl]-urea;
N-(5-{4-[3-(5-tert-Butyl-2-methoxy-phenyl)-ureido]-naphthalen-1-yl}-pyridin-2-yl)-acetamide;
N-(5-tert-Butyl-2-methoxy-3-{3-[4-(6-morpholin-4-ylmethyl-pyridin-3-yl)-naphthalen-1-yl]ureido}-phenyl)-N-methyl-acetamide;
N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;
1-(5-tert-Butyl-2-methoxy-phenyl)-3-{4-[6-(pyridin-3-yloxy)-pyridin-3-yl]-naphthalen-1-yl}-urea;
[4-(6-Morpholin-4-ylmethyl-pyridin-3-yl)-naphthalen-1-yl]-carbamic acid 3-tert-butyl-phenyl ester;

N-(5-tert-Butyl-2-methoxy-3-{3-[4-(6-morpholin-4-ylm-ethyl-pyridin-3-yl)-naphthalen-1-yl]-ureido}-phenyl)-methanesulfonamide and the pharmaceutically acceptable derivatives thereof.

In addtion to the abovementioned compounds the following prophetic compounds of the formula(III) may be useful in the novel methods described herein:

1-(5-tert-Butyl-2-methylsulfanyl-pyridin-3-yl)-3-[4-(6-morpholin-4-ylmethyl-pyridin-3-yl)-naphthalen-1-yl]-urea;

1-(5-tert-Butyl-2-chloro-pyridin-3-yl)-3-[4-(6-morpholin-4-ylmethyl-pyridin-3-yl)-naphthalen-1-yl]-urea;

1-(5-tert-Butyl-2-methylamino-pyridin-3-yl)-3-[4-(6-morpholin-4-ylmethyl-pyridin-3-yl)-naphthalen-1-yl]-urea;

N-(5-tert-Butyl-3-{3-[4-(6-morpholin-4-ylmethyl-pyridin-3-yl)-naphthalen-1-yl]-ureido}-2-oxo-2H-pyridin-1-yl)-methanesulfonamide;

5-tert-Butyl-7-{3-[4-(6-morpholin-4-ylmethyl-pyridin-3-yl)-naphthalen-1-yl]-ureido}-benzooxazole-2-carboxylic acid amide;

2-(5-tert-Butyl-7-{3-[4-(6-morpholin-4-ylmethyl-pyridin-3-yl)-naphthalen-1-yl]-ureido}-benzooxazol-2-yl)-acetamide;

5-tert-Butyl-2-methoxy-3-{3-[4-(6-morpholin-4-ylmethyl-pyridin-3-yl)-naphthalen-1-yl]-ureido}-benzamide and the pharmaceutically acceptable derivatives thereof.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I), (Ia), (II) and (III) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl" shall be understood to mean an aromatic 5–8 membered monocyclic or 8–11 membered bicyclic ring containing 1–4 heteroatoms such as N, O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl.

The invention includes methods of using pharmaceutically acceptable derivatives of compounds of formula (I), (Ia), (II) and (III). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formulas (I), (Ia), (II) or (III).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$–$C_4$ alkyl$)_4^+$ salts.

In addition, within the scope of the invention is use of prodrugs of compounds of the formula (I), (Ia), (II) and (III). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Methods of Use

In accordance with the invention, there are provided novel methods of using the compounds of the formulas (I), (Ia), (II) and (III). as described in WO 00/55139 and U.S.

application Ser. No. 09/505,582. The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are described in WO 00/55139 as being useful for the treatment of the following conditions and diseases: osteoarthritis, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

Suprisingly, it has been discovered for the first time that the compounds disclosed in WO 00/55139 are useful in methods for treating: acute and chronic inflammation in the lung caused by inhalation of smoke, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease and congestive heart failure.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822 and PCT/US 01/21860 each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formulas (I), (Ia), (II) and (III) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The compounds described hereinabove may be prepared by Method A, B, or C as illustrated in Scheme I, preferably method C, in WO 00/55139. Starting materials used are either commercially available or easily prepared from commercially available materials known by those skilled in the art. Further reference in this regard may be made to U.S. application Ser. Nos. 09/505,582, 09/484,638, 09/714,539, 09/611,109, 09/698,442 and U.S. provisional application No. 60/216,283. Each of the aforementioned incorporated herein by reference in their entirety.

Assessment of Biological Properties

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation,* 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E.coli* serotype 0111.B4; stored as 1 mg/ml stock in endotoxin screened distilled $H_2O$ at −80° C.). Blanks (unstimulated) received H₂O vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Preferred compounds including those from the synthetic examples above were evaluated and had $IC_{50}$<10 uM in this assay.

Inhibition of other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

What is claimed is:

1. A method of treating chronic obstructive pulmonary disease, said method comprising administering to a patient in need of such treatment a therapeutically effective amount of a compound of the formula (III):

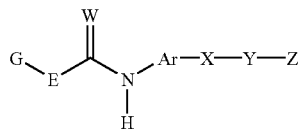

wherein:

E is carbon or a heteroatom group chosen from —O—, —NH— and —S—;

G is:
an aromatic $C_{6-10}$ carbocycle or a nonaromatic $C_{3-10}$ carbocycle saturated or unsaturated;
a 6–14 membered monocyclic, bicyclic or tricyclic heteroaryl containing 1 or more heteroatoms chosen from O, N and S;
a 6–8 membered monocyclic heterocycle containing one or more heteroatoms chosen from O, N and S; or
an 8–11 membered bicyclic heterocycle, containing one or more heteroatoms chosen from O, N and S;
wherein G is optionally substituted by one or more $R_1$, $R_2$ or $R_3$;

Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:
a bond or a $C_{1-4}$ saturated or unsaturated branched or unbranched carbon chain optionally partially or fully halogenated, wherein one or more C atoms are optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is:
aryl, heteroaryl selected from pyridinyl, piperazinyl, pyrimidinyl, pyridazinyl, pyrazinyl, imidazolyl, pyrazolyl, triazolyl, tetrazolyl, furanyl, thienyl and pyranyl, heterocycle selected from tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl) amino; or Z is optionally substituted with one to three amino or amino-$C_{1-3}$ alkyl wherein the N atom is optionally independently mono- or di-substituted by amino $C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy; or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, halogen, nitrile, amino wherein the N atom is optionally independently mono- or di-substituted by $C_{1-3}$acyl, $C_{1-6}$alkyl or $C_{1-3}$alkoxy$C_{1-3}$alkyl, $C_{1-6}$alkyl branched or unbranched, $C_{1-6}$alkoxy, $C_{1-3}$acylamino, nitrile$C_{1-4}$alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:
$C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl, pyridinyl, pyrimidinyl, pyrazinyl, pyridazinyl, pyrrolyl, pyrrolidinyl, imidazolyl, pyrazolyl, thienyl, furyl, dioxolanyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl)amino, and mono- or di($C_{1-3}$alkyl)aminocarbonyl;

or $R_1$ is cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy $C_{1-3}$alkyl or aryl; or an analog of such cycloalkyl group wherein one to three ring methylene groups are independently replaced by O, $S(O)_m$, CHOH, >C=O, >C=S or NH;

phenyloxy or benzyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloaryl group wherein one to two ring methyne groups are independently replaced by N;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three $C_{1-3}$ alkyl optionally partially or fully halogenated, nitrile, hydroxy$C_{1-3}$alkyl or aryl; or an analog of such cycloalkyl group wherein one to three ring methylene groups are independently replaced by O, $S(O)_m$, CHOH, >C=O, >C=S or NH;

$C_{3-10}$ branched or unbranced alkenyl each being optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with one to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di($C_{1-3}$alkyl)aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

oxo, nitrile, halogen;

silyl containing three $C_{1-4}$ alkyl groups optionally partially or fully halogenated; or $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, halogen, methoxycarbonyl, $C_{1-3}$ alkyl-$S(O)_m$ optionally partially or fully halogenated, or phenyl-$S(O)_m$;

$OR_6$, $C_{1-6}$ alkoxy, hydroxy, nitrile, nitro, halogen;

or amino-$S(O)_m$— wherein the N atom is optionally independently mono- or di-substituted by $C_{1-6}$alkyl or aryl$C_{0-3}$alkyl, or amino wherein the N atom is optionally independently mono- or di-substituted by $C_{1-3}$alkyl, aryl$C_{0-3}$alkyl, $C_{1-6}$acyl, $C_{1-6}$alkyl-$S(O)_m$— or aryl$C_{0-3}$alkyl-$S(O)_m$—, each of the aforementioned alkyl and aryl in this subparagraph are optionally partially or fully halogenated and optionally substituted with one to two $C_{1-6}$ alkyl or $C_{1-6}$ alkoxy;

each $R_3$ is independently:

phenyl, naphthyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$ alkyl)amino, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-$(C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-$(C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-$(C_{1-3})$alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally be partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-$(C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$—, $R_{23}R_{24}NC(O)$—$C_{1-3}$alkoxy or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, S(O)$_m$ and wherein said alkynyl group is optionally independently substituted with one to two oxo groups, pyrroldinyl, pyrrolyl, morpholino, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl)amino optionally substituted by one or more halogen atoms;

$C_{1-6}$acyl or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently: nitrile, phenyl, morpholino, piperidinyl, piperazinyl, imidazolyl, pyridinyl, tetrazolyl, amino or mono- or di-$(C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}$, $R_{23}$ and $R_{24}$ is independently:

hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-$(C_{1-3}$ alkyl)aminocarbonyl, phenyl, pyridinyl, amino or mono- or di-$(C_{1-4}$alkyl)amino each of which is optionally partially or fully halogenated and optionally substituted with mono- or di-$(C_{1-3}$alkyl)amino; or $R_{23}$ and $R_{24}$ taken together optionally form a heterocyclic or heteroaryl ring;

m=0, 1 or 2;

W is O or S and the pharmaceutically acceptable salts thereof.

2. The method according to claim 1 wherein

E is —CH$_2$—, —NH— or —O—;

W is O; and

G is:

phenyl, naphthyl, benzocyclobutanyl, dihydronaphthyl, tetrahydronaphthyl, benzocycloheptanyl, benzocycloheptenyl, indanyl, indenyl;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, 2,3-dihydro- 1H-indolyl, indolinyl, indolonyl, indolinonyl, phthalimidyl, chromoyl;

oxetanyl, pyrrolidinyl, tetrahydrofuranyl, tetrahydrothiophenyl, piperidinyl, piperazinyl, morpholino, tetrahydropyranyl, dioxanyl, tetramethylene sulfonyl, tetramethylene sulfoxidyl, oxazolinyl, 3,4-dihydro-2H-benzo[1,4]oxazinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholino, thiazolidinyl, dihydrooxazinyl, dihydropyranyl, oxocanyl, heptacanyl, thioxanyl or dithianyl; wherein G is optionally substituted by one or more $R_1$, $R_2$ or $R_3$.

3. The method according to claim 2 wherein

E is —NH—;

G is phenyl, pyridinyl, pyridonyl, naphthyl, quinolinyl, isoquinolinyl, pyrazinyl, benzimidazolyl, benzooxazolyl, benzooxazolonyl, benzofuranyl, benzothiophenyl, benzpyrazolyl, dihydrobenzofuranyl, dihydrobenzothiophenyl, 3,4-dihydro-2H-benzo[1,4]oxazinyl, indanyl, indenyl, indolyl, indolinyl, indolonyl, 2,3-dihydro-1H-indolyl or indolinonyl, wherein G is optionally substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$alkyl)amino, mono- or di-($C_{1-3}$ alkylamino) carbonyl, $NH_2C(O)$, $C_{1-6}$ alkyl-$S(O)_m$ or halogen;

Y is:

a bond or a $C_{1-4}$ saturated or unsaturated carbon chain wherein one or more of the C atoms is optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is: phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-aza-bicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl) amino, $CONH_2$ or OH; or Z is optionally substituted by phenyl, heterocycle or heteroaryl as hereinabove described in this paragraph each in turn is optionally substituted by halogen, $C_{1-3}$ alkyl or $C_{1-3}$ alkoxy;

or Z is nitrile, nitrile$C_{1-3}$ alkyl, $C_{1-6}$ alkyl-$S(O)_m$, halogen, hydroxy, $C_{1-3}$ alkyl, $C_{1-3}$ acylamino, $C_{1-4}$ alkoxy, amino, mono- or di-($C_{1-3}$ alkyl)aminocarbonyl, or amino mono or di-substituted by amino$C_{1-6}$ alkyl or $C_{1-3}$alkoxy$C_{1-3}$alkyl;

each $R_1$ is independently:

$C_{1-6}$ alkyl branched or unbranched optionally partially or fully halogenated, wherein one or more C atoms are optionally independently replaced by O, N or $S(O)_m$, and wherein said $C_{1-6}$ alkyl is optionally substituted with one to three $C_{3-6}$cycloalkyl, oxo, phenyl, dioxolanyl, pyrrolidinyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile and $C_{1-3}$alkoxy which is optionally partially or fully halogenated; cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; or an analog of such cycloalkyl group wherein one to three ring methylene groups are independently replaced by O, S, CHOH, >C=O, >C=S or NH;

oxo;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms; or silyl containing three $C_{1-4}$ alkyl groups optionally partially or fully halogenated;

$R_2$ is independently:

a $C_{1-5}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-2}$ alkyl-$S(O)_m$ optionally partially or fully halogenated, or phenyl-$S(O)_m$;

$C_{1-3}$ alkoxy, hydroxy, nitrile, nitro, halogen;

or amino-$S(O)_m$— wherein the N atom is optionally independently mono- or di-substituted by $C_{1-3}$alkyl or aryl$C_{0-3}$alkyl, or amino wherein the N atom is optionally independently mono- or di-substituted by $C_{1-3}$alkyl, aryl$C_{0-3}$alkyl, $C_{1-3}$acyl, $C_{1-4}$alkyl-$S(O)_m$— or aryl$C_{0-3}$alkyl-$S(O)_m$, each of the aforementioned alkyl and aryl in this subparagraph are optionally partially or fully halogenated and optionally substituted with one to two $C_{1-3}$ alkyl or $C_{1-3}$ alkoxy;

$R_3$ is independently:

phenyl, morpholino, pyridinyl, pyrimidinyl, pyrazinyl, pyrrolyl, pyrrolidinyl, imidazolyl, [1,3,4]oxadiazol, pyrazolyl, each is optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkoxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, mono- or di-($C_{1-3}$alkyl)amino, mono- or di-($C_{1-3}$)alkylamino-$C_{1-5}$ alkyl, mono- or di-($C_{1-3}$alkyl)amino-$S(O)_2$, $R_7$—$C_{1-5}$ alkyl, $R_8$—$C_{1-5}$alkoxy, $R_9$—C(O)—$C_{1-5}$ alkyl, $R_{10}$— $C_{1-5}$ alkyl($R_{11}$)N, carboxy-mono- or di-($C_{1-5}$)-alkyl-amino;

$C_{1-3}$ alkyl or $C_{1-4}$ alkoxy each being optionally partially or fully halogenated or optionally substituted with $R_{17}$;

$OR_{18}$ or $C_{1-6}$ alkyl optionally substituted with $OR_{18}$;

amino or mono- or di-($C_{1-5}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$—, $R_{23}R_{24}NC(O)$—$C_{1-2}$alkoxy or $R_{26}C(O)CH_2N(R_{21})$—;

$C_{2-4}$alkenyl substituted by $R_{23}R_{24}NC(O)$—; or $C_{24}$ alkynyl branched or unbranched carbon chain optionally partially or fully halogenated wherein one of the methylene groups is optionally replaced by O, and optionally independently substituted with one to two oxo groups, pyrroldinyl, pyrrolyl, morpholino, piperidinyl, piperazinyl, imidazolyl, phenyl, pyridinyl, tetrazolyl or one or more $C_{1-4}$ alkyl optionally substituted by one or more halogen atoms;

$C_{1-3}$acyl; and $R_{23}$ and $R_{24}$ taken together optionally form imidazolyl, piperidinyl, morpholino, piperazinyl or a pyridinyl ring.

4. The method according to claim 3 wherein:

G is phenyl, pyridinyl, pyridonyl, naphthyl, quinolinyl, isoquinolinyl, pyrazinyl, 3,4-dihydro-2H-benzo[1,4]oxazinyl, benzothiophenyl, dihydrobenzofuranyl, dihydrobenzothiophenyl, benzooxazolyl, indanyl, indolyl, indolinyl, indolonyl or indolinonyl, wherein G is optionally substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$alkylamino) carbonyl, $NH_2C(O)$, $C_{1-6}$ alkyl-$S(O)_m$ or halogen;

Y is:

a bond or a $C_{1-4}$ saturated carbon chain wherein one or more of the C atoms is optionally replaced by O, N or S and wherein Y is optionally independently substituted with nitrile or oxo;

Z is:

phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo[2.2.1]heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy; or Z is hydroxy, $C_{1-3}$ alkyl, $C_{1-3}$ alkoxy, $C_{1-3}$ acylamino, $C_{1-3}$ alkylsulfonyl, nitrile $C_{1-3}$ alkyl or amino mono or di-substituted by $C_{1-3}$ alkoxy$C_{1-3}$ alkyl;

each $R_1$ is independently:

$C_{1-5}$ alkyl branched or unbranched optionally partially or fully halogenated, wherein one or more C atoms are optionally independently replaced by O, N or $S(O)_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O;

oxo;

$C_{2-4}$ alkynyl optionally partially or fully halogenated wherein one or more methylene groups are optionally replaced by O, and optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms; or silyl containing three $C_{1-2}$ alkyl groups optionally partially or fully halogenated;

each $R_2$ is independently:

a $C_{1-4}$ alkyl optionally partially or fully halogenated, $C_{1-4}$ alkoxy optionally partially or fully halogenated, bromo, chloro, fluoro, methoxycarbonyl, methyl-$S(O)_m$, ethyl-$S(O)_m$ each optionally partially or fully halogenated or phenyl-$S(O)_m$;

or $R_2$ is mono- or di-$C_{1-3}$acylamino, amino-$S(O)_m$ or $S(O)_m$amino wherein the N atom is mono- or di-substituted by $C_{1-3}$alkyl or phenyl, nitrile, nitro or amino;

each $R_3$ is independently:

phenyl, morpholino, pyridinyl, pyrimidinyl, pyrrolidinyl, 2,5-pyrrolidin-dionyl, imidazolyl, [1,3,4]oxadiazol, pyrazolyl, each of the aforementioned is optionally substituted with one to three $C_{1-3}$ alkyl which is optionally partially or fully halogenated, halogen, oxo, hydroxy, nitrile and $C_{1-3}$ alkoxy optionally partially or fully halogenated;

$C_{1-3}$ alkyl or $C_{1-3}$ alkoxy optionally partially or fully halogenated or optionally substituted with $R_{17}$;

$OR_{18}$ or $C_{1-3}$ alkyl optionally substituted with $OR_{18}$;

amino or mono- or di-($C_{1-3}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl;

$C_{1-3}$acyl and $R_{23}$ and $R_{24}$ taken together optionally form morpholino.

5. The method according to claim 4 wherein

G is phenyl, pyridinyl, pyridonyl, 2-naphthyl, quinolinyl, isoquinolinyl, dihydrobenzofuranyl, indanyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl, indolinyl, indolonyl, or indolinonyl , wherein G is optionally substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or

—$CH_2$—, —$CH_2CH_2$—, —$C(O)$—, —$O$—, —$S$—, —$NH$—$CH_2CH_2CH_2$—, —$N(C\ H_3)$—, $CH_2(CN)CH_2$—$NH$—$CH_2$ or —$NH$—;

Z is morpholino, dioxolanyl, tetrahydrofuranyl, pyridinyl, 2-oxa-5-aza-bicyclo[2.2.1]heptanyl, $C_{1-3}$alkoxyphenylpiperazinyl, hydroxy, $C_{1-3}$alkyl, N,N-di$C_{1-3}$alkoxy$C_{1-3}$alkylamino, $C_{1-3}$acylamino, $C_{1-3}$alkylsulfonyl or nitrile$C_{1-3}$alkyl;

each $R_1$ is independently:

$C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$alkoxy;

cyclopropyl, cyclopentanyl, cyclohexanyl and bicyclopentanyl optionally substituted with one to three methyl groups optionally partially or fully halogenated, nitrile, hydroxymethyl or phenyl; or 2-tetrahydrofuranyl substituted by methyl; or trimethyl silyl;

propynyl substituted hydroxy or tetrahydropyran-2-yloxy;

$R_2$ is is mono- or di-$C_{1-3}$acylamino, amino-$S(O)_m$ or $S(O)_m$ amino wherein the N atom is mono- or di-substituted by $C_{1-3}$alkyl or phenyl, bromo, chloro, fluoro, nitrile, nitro, amino, methylsulfonyl optionally partially or fully halogenated or phenylsulfonyl;

each $R_3$ is independently:

phenyl, morpholino, pyridinyl, pyrimidinyl, pyrrolidinyl, 2,5-pyrrolidin-dionyl, imidazolyl, [1,3,4]oxadiazol or pyrazolyl, each is optionally substituted with $C_{1-2}$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;

$C_{2-4}$alkenyl substituted by $R_{23}R_{24}NC(O)$—; or $C_{2-4}$ alkynyl substituted with pyrroldinyl or pyrrolyl;

$C_{1-2}$acyl; and $R_{23}$ and $R_{24}$ are H or $R_{23}$ and $R_{24}$ taken together optionally form morpholino; and $R_{26}$ is morpholino.

6. The method according to claim 5 wherein

G is phenyl, pyridinyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro- 1H-indol-5-yl or 2-naphthyl wherein G is optionally substituted by one or more $R_1$, $R_2$ or $R_3$;

X is:

imidazolyl, pyridinyl, pyrimidinyl or pyrazinyl;

Y is:

a bond, $CH_2(CN)CH_2$—NH—$CH_2$, —$CH_2$—, —NH—$CH_2CH_2CH_2$— or —NH—;

Z is morpholin-4yl, dioxolan-2yl, tetrahydrofuranyl, pyridinyl, 2-oxa-5-aza-bicyclo[2.2.1]hept-5yl, methoxyphenylpiperazinyl, hydroxy, methyl, N,N-dimethoxyethylamino, acetylamino, methylsulfonyl or cyanoethyl;

each $R_1$ is independently:

tert-butyl, sec-butyl, tert-amyl, phenyl, tetrahydropyran-2-yloxypropynyl, hydroxypropynyl, trihalomethyl, 2,2-diethylpropionyl or cyclohexanyl;

$R_2$ is chloro, nitro, amino, nitrile, methylsulfonylamino, diacetylamino, phenylsulfonylamino, N,N-di(methylsulfonyl)amino, methylsulfonyl or trihalomethylsulfonyl;

$R_3$ is independently:

methyl, $C_{1-3}$ alkoxy, methoxymethyl, hydroxypropyl, dimethylamino, $C_{1-4}$alkylamino, $NH_2C(O)$methoxy, acetyl, pyrrolidinyl, imidazolyl, pyrazolyl, morpholino or morpholinocarbonyl.

7. The method according to claim 6 wherein
X is pyridinyl.

8. The method according to claim 7 wherein
the pyridinyl is attached to Ar via the 3-pyridinyl position.

9. A method of treating chronic obstructive pulmonary disease,
said method comprising administering to a patient in need of such treatment a therapeutically effective amount of a compound chosen from:

1-(4-tert-Butyl-phenyl)-3-[4-(6-morpholin-4-ylmethyl-pyridin-3-yl)-naphthalen-1-yl]-urea;

1-(5-tert-Butyl-2-methyl-phenyl)-3-[4-(4-morpholin-4-ylmethyl-piperidin-1-yl)-naphthalen-1-yl]-urea;

1-(6-Chloro-4-trifluoromethyl-pyridin-2-yl)-3-[4-(6-morpholin-4-ylmethyl-pyridin-3-yl)-naphthalen-1-yl]-urea;

1-(4-Difluoromethoxy-phenyl)-3-[4-(6-morpholin-4-ylmethyl-pyridin-3-yl)-naphthalen-1-yl]-urea;

1-(3-Methyl-naphthalen-2-yl)-3-[4-(6-morpholin-4-ylmethyl-pyridin-3-yl)-naphthalen-1-yl]-urea;

1-[2-Methoxy-5-(1-methyl-1-phenyl-ethyl)-phenyl]-3-[4-(6-morpholin-4-ylmethyl-pyridin-3-yl)-naphthalen-1-yl]-urea;

(5-tert-Butyl-2-methyl-phenyl)-carbamic acid 3-(5-{4-[3-(5-tert-butyl-2-methyl-phenyl)-ureido]-naphthalen-1-yl}-pyridin-2-ylamino)-propyl ester;

1-(6-tert-Butyl-benzo[1,3]dioxol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1,3-Bis-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-hydroxy-phenyl]-3-[4-(6-morpholin-4-ylmethyl-pyridin-3-yl)-naphthalen-1-yl]-urea;

1-[5-tert-Butyl-2-(2-pyrrolidin-1-yl-ethoxy)-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(2-p-tolyloxy-5-trifluoromethyl-phenyl)-urea;

1-[2-(2-Methoxy-phenoxy)-5-trifluoromethyl-phenyl]-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-naphthalen-1-yl-urea;

1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-{5-tert-Butyl-2-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-(5-Hydroxymethyl-2-methyl-phenyl)-3-[4-(6-morpholin-4-ylmethyl-pyridin-3-yl)-naphthalen-1-yl]-urea;

1-(2-Methoxy-dibenzofuran-3-yl)-3-[4-(6-morpholin-4-ylmethyl-pyridin-3-yl)-naphthalen-1-yl]-urea;

1-(2,5-Di-tert-butyl-phenyl)-3-[4-(6-morpholin-4-ylmethyl-pyridin-3-yl)-naphthalen-1-yl]-urea;

1-[3-(4-Bromo-1-methyl-1H-pyrazol-3-yl)-phenyl]-3-[4-(6-morpholin-4-ylmethyl-pyridin-3-yl)-naphthalen-1-yl]-urea;

1-(3-Hydroxy-5,6,7,8-tetrahydro-naphthalen-2-yl)-3-[4-(6-morpholin-4-ylmethyl-pyridin-3-yl)-naphthalen-1-yl]-urea;

1-(1-Acetyl-2,3-dihydro-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-oxazol-5-yl-phenyl)-urea;

1-[4-(6-Morpholin-4-ylmethyl-pyridin-3-yl)-naphthalen-1-yl]-3-(3-[1,3,4]oxadiazol-2-yl-phenyl)-urea;

1-(2-Methoxy-5-trifluoromethyl-phenyl)-3-[4-(6-morpholin-4-ylmethyl-pyridin-3-yl)-naphthalen-1-yl]-urea;

Furan-2-carboxylic acid (4-tert-butyl-2-{3-[4-(6-morpholin-4-ylmethyl-pyridin-3-yl)-naphthalen-1-yl]-ureido}-phenyl)-amide;

1-(2-Methoxy-4-phenylamino-phenyl)-3-[4-(6-morpholin-4-ylmethyl-pyridin-3-yl)-naphthalen-1-yl]-urea;

1-(5-Methoxy-2-methyl-phenyl)-3-[4-(6-morpholin-4-ylmethyl-pyridin-3-yl)-naphthalen-1-yl]-urea;

1-(3-Hydroxy-naphthalen-2-yl)-3-[4-(6-morpholin-4-ylmethyl-pyridin-3-yl)-naphthalen-1-yl]-urea;

N,N-Diethyl-4-methoxy-3-{3-[4-(6-morpholin-4-ylmethyl-pyridin-3-yl)-naphthalen-1-yl]-ureido}-benzenesulfonamide;

1-(2,2-Difluoro-benzo[1,3]dioxol-5-yl)-3-[4-(6-morpholin-4-ylmethyl-pyridin-3-yl)-naphthalen-1-yl]-urea;

1-[5-(1,1-Dimethyl-propyl)-2-phenoxy-phenyl]-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]-urea;

2-Chloro-5-{3-[4-(6-morpholin-4-ylmethyl-pyridin-3-yl)-naphthalen-1-yl]-ureido}-benzoic acid isopropyl ester;

1-(4-Amino-3,5-dibromo-phenyl)-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

2-(5-tert-Butyl-2-methoxy-phenyl)-N-[4-(6-morpholin-4-ylmethyl-pyridin-3-yl)-naphthalen-1-yl]-acetamide;

1-(2-Methoxy-5-phenoxy-phenyl)-3-[4-(6-morpholin-4-ylmethyl-pyridin-3-yl)-naphthalen-1-yl]-urea;

1-(3,3-Dimethyl-2-oxo-2,3-dihydro-1H-indol-7-yl)-3-[4-(6-morpholin-4-ylmethyl-pyridin-3-yl)-naphthalen-1-yl]-urea;

1-(5-tert-Butyl-2-cyclopentyloxy-phenyl)-3-[4-(6-morpholin-4-ylmethyl-pyridin-3-yl)-naphthalen-1-yl]-urea;

1-(5-tert-Butyl-2-methoxy-phenyl)-3-{4-[6-(3-pyridin-3-yl-pyrrolidin-1-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(6-tert-Butyl-3-oxo-3,4-dihydro-2H-benzo[1,4]oxazin-7-yl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-[6-tert-Butyl-4-(2-morpholin-4-yl-ethyl)-3-oxo-3,4-dihydro-2H-benzo[1,4]oxazin-8-yl]-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

N-(5-tert-Butyl-2-methoxy-4-{3-[4-(6-morpholin-4-ylmethyl-pyridin-3-yl)-naphthalen-1-yl]-ureido}-phenyl)-methanesulfonamide;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-(2-Ethanesulfonyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(3-dimethylamino-pyrrolidin-1-ylmethyl)-pyridin-3-yl]-naphthalen-1-yl}-urea;

N-[1-(5-{4-[3-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-{3-[4-(6-morpholin-4-ylmethyl-pyridin-3-yl)-naphthalen-1-yl]-ureido}-phenyl)-isobutyramide;

2-(4-tert-Butyl-2-{3-[4-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(6-tert-Butyl-3-cyano-2-methoxymethoxy-pyridin-4-yl)-3-[4-(6-morpholin-4-ylmethyl-pyridin-3-yl)-naphthalen-1-yl]-urea;

1-(6-tert-Butyl-3-cyano-2-hydroxy-pyridin-4-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(1,3,3-trimethyl-2,3-dihydro-1H-indol-5-yl)-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(4-morpholin-4-ylmethyl-piperidin-1-yl)-naphthalen-1-yl]-urea;

1-[5-tert-Butyl-2-(1-methyl-1H-pyrazol-4-yl)-phenyl]-3-[4-(4-morpholin-4-ylmethyl-piperidin-1-yl)-naphthalen-1-yl]-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-3-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

N-(5-{4-[3-(5-tert-Butyl-2-methyl-phenyl)-ureido]-naphthalen-1-yl}-pyrazin-2-yl)-methanesulfonamide;

1-[4-(6-{[Bis-(2-cyano-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;

1-(5-tert-Butyl-2-methoxy-phenyl)-3-{4-[6-(2-methoxymethyl-morpholin-4-ylmethyl)-pyridin-3-yl]-naphthalen-1-yl}-urea;

1-(5-tert-Butyl-2-methoxy-phenyl)-3-(4-{6-[(2-morpholin-4-yl-ethylamino)-methyl]-pyridin-3-yl}-naphthalen-1-yl) -urea;

1-(5-tert-Butyl-2-methoxy-phenyl)-3-{4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-{4-[3-(5-tert-Butyl-2-methoxy-phenyl)-ureido]-naphthalen-1-yl}-pyridin-2-ylmethyl)-piperidine-4-carboxylic acid amide;

1-(5-tert-Butyl-2-methoxy-phenyl)-3-{4-[6-(1-oxo-1l4-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-{4-[6-(4-Acetyl-piperazin-1-ylmethyl)-pyridin-3-yl]-naphthalen-1-yl}-3-(5-tert-butyl-2-methoxy-phenyl)-urea;

4-(5-{4-[3-(5-tert-Butyl-2-methoxy-phenyl)-ureido]-naphthalen-1-yl}-pyridin-2-ylmethyl)-piperazine-1-carboxylic acid ethyl ester;

1-(5-tert-Butyl-2-methoxy-phenyl)-3-(4-{6-[(2-pyridin-3-yl-ethylamino)-methyl]-pyridin-3-yl}-naphthalen-1-yl)-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-(4-{6-[(2-methylsulfanyl-ethylamino)-methyl]-pyridin-3-yl}-naphthalen-1-yl)-urea;

1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-tert-Butyl-2-methoxy-phenyl)-3-(4-{6-[(2-piperazin-1-yl-ethylamino)-methyl]-pyridin-3-yl}-naphthalen-1-yl)-urea;

1-(5-tert-Butyl-2-methoxy-phenyl)-3-{4-[6-(4-pyrimidin-2-yl-piperazin-1-ylmethyl)-pyridin-3-yl]-naphthalen-1-yl}-urea;

1-(5-tert-Butyl-2-methoxy-phenyl)-3-{4-[6-(4-pyridin-2-yl-piperazin-1-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-{4-[6-(2-thia-5-aza-bicyclo[2.2.1]hept-5-ylmethyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

1-(5-tert-Butyl-2-methoxy-phenyl)-3-{4-[6-(pyridin-3-ylamino)-pyridin-3-yl]-naphthalen-1-yl}-urea;

[4-(6-Morpholin-4-ylmethyl-pyridin-3-yl)-naphthalen-1-yl]-carbamic acid 3-tert-butyl-phenyl ester and N-(5-tert-Butyl-2-methoxy-3-{3-[4-(6-morpholin-4-ylmethyl-pyridin-3-yl)-naphthalen-1-yl]-ureido}-phenyl)-methanesulfonamide or the pharmaceutically acceptable salts thereof.

10. A method of treating chronic obstructive pulmonary disease said method comprising administering to a patient in need of such treatment a therapeutically effective amount of a compound chosen from:

1-(3-Methyl-naphthalen-2-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-(2-Methoxy-5-trifluoromethyl-phenyl)-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl}-pyridin-3-yl)-naphthalen-1-yl]-3-(5-tert-butyl-2-methoxyphenyl)-urea;
N-[1-(5-{4-[3-(5-tert-Butyl-2-methoxy-phenyl)-ureido]-naphthalen-1-yl}-pyridin-2-ylmethyl)-pyrrolidin-3-yl]-acetamide;
1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-propionamide;
1-(5-tert-Butyl-2-methyl-benzooxazol-7-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3-trifluoromethanesulfonyl-phenyl)-urea;
N-(5-tert-Butyl-2-methoxy-3-{3-[4-(6-morpholin-4-ylmethyl-pyridin-3-yl)-naphthalen-1-yl]-ureido}-phenyl)-isobutyramide;
2-(4-tert-Butyl-2-{3-[4-(6-morpholin-4-ylmethyl-pyridin-3-yl)-naphthalen-1-yl]-ureido}-phenoxy)-acetamide;
1-(5-tert-Butyl-2-oxo-2,3-dihydro-benzooxazol-7-yl)-3-[4-(6-morpholin-4-ylmethyl-pyridin-3-yl)-naphthalen-1-yl]-urea;
1-(5-tert-Butyl-3-cyano-2-methoxy-phenyl)-3-[4-(6-morpholin-4-ylmethyl-pyridin-3-yl)-naphthalen-1-yl]-urea;
1-(5-tert-Butyl-benzooxazol-7-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-benzenesulfonamide;
Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
1-(5-tert-Butyl-2-methoxy-phenyl)-3-[4-(2-morpholin-4-ylmethyl-pyrimidin-5-yl)-naphthalen-1-yl]-urea;
1-(5-tert-Butyl-2-methylsulfanyl-phenyl)-3-[4-(6-morpholin-4-ylmethyl-pyridin-3-yl)-naphthalen-1-yl]-urea;
1-(5-tert-Butyl-2-methoxy-pyridin-3-yl)-3-[4-(6-morpholin-4-ylmethyl-pyridin-3-yl)-naphthalen-1-yl]-urea;
2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
N-(5-{4-[3-(5-tert-Butyl-2-methyl-phenyl)-ureido]-naphthalen-1-yl}-pyrazin-2-yl)-methanesulfonamide;
1-[4-(6-{[Bis-(2-cyano-ethyl)-amino]-methyl}-pyridin-3-yl)-naphthalen-1-yl]-3-(5-tert-butyl-2-methoxy-phenyl)-urea;
1-(5-tert-Butyl-2-methoxy-phenyl)-3-{4-[6-(4-methyl-piperazin-1-ylmethyl)-pyridin-3-yl]-naphthalen-1-yl}-urea;
1-(5-tert-Butyl-2-methoxy-phenyl)-3-[4-(6-thiomorpholin-4-ylmethyl-pyridin-3-yl)-naphthalen-1-yl]-urea;
1-(5-tert-Butyl-2-methoxy-phenyl)-3-{4-[6-(2,6-dimethyl-piperidin-1-ylmethyl)-pyridin-3-yl]-naphthalen-1-yl}-urea;
1-(5-tert-Butyl-2-methoxy-phenyl)-3-{4-[6-(1-oxo-tetrahydro-thiopyran-4-ylamino)-pyridin-3-yl]-naphthalen-1-yl}-urea;
1-(5-tert-Butyl-2-methoxy-phenyl)-3-{4-[6-(tetrahydro-pyran-4-ylamino)-pyridin-3-yl]-naphthalen-1-yl}-urea;
1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;
1-(5-tert-Butyl-2-methoxy-phenyl)-3-{4-[6-(2-methoxymethyl-morpholin-4-ylmethyl)-pyridin-3-yl]-naphthalen-1-yl}-urea;
1-(5-tert-Butyl-2-methoxy-phenyl)-3-{4-[6-(2-methyl-3-oxo-piperazin-1-ylmethyl)-pyridin-3-yl]-naphthalen-1-yl}-urea;
1-(5-{4-[3-(5-tert-Butyl-2-methoxy-phenyl)-ureido]-naphthalen-1-yl}-pyridin-2-ylmethyl)-piperidine-3-carboxylic acid amide;
1-(5-tert-Butyl-2-methoxy-phenyl)-3-{4-[6-(1-oxo-1l4-thiomorpholin-4-ylmethyl)-pyridin-3-yl]-naphthalen-1-yl}-urea;
1-(3,3-Dimethyl-2-oxo-2,3-dihydro-1H-indol-5-yl)-3-[4-(6-morpholin-4-ylmethyl-pyridin-3-yl)-naphthalen-1-yl]-urea;
1-(5-tert-Butyl-2-methoxy-phenyl)-3-{4-[6-(3-oxo-piperazin-1-ylmethyl)-pyridin-3-yl]-naphthalen-1-yl}-urea;
1-(5-tert-Butyl-2-methoxy-phenyl)-3-(4-{6-[(tetrahydro-furan-3-ylamino)-methyl]-pyridin-3-yl}-naphthalen-1-yl)-urea;
1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;
1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;
1-(5-tert-Butyl-2-methoxy-phenyl)-3-{4-[6-(2,6-dimethyl-morpholin-4-ylmethyl)-pyridin-3-yl]-naphthalen-1-yl}-urea;
1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;
1-(5-tert-Butyl-2-methoxy-phenyl)-3-{4-[6-(morpholine-4-carbonyl)-pyridin-3-yl]-naphthalen-1-yl}-urea;
1-(5-tert-Butyl-2-methoxy-phenyl)-3-[4-(5-morpholin-4-ylmethyl-pyrazin-2-yl)-naphthalen-1-yl]-urea;
1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;
1-(3-Amino-5-tert-butyl-2-methoxy-phenyl)-3-[4-(6-morpholin-4-ylmethyl-pyridin-3-yl)-naphthalen-1-yl]-urea;
N-(5-{4-[3-(5-tert-Butyl-2-methoxy-phenyl)-ureido]-naphthalen-1-yl}-pyridin-2-yl)-acetamide;
N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;
N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;
1-(5-tert-Butyl-2-methoxy-phenyl)-3-{4-[6-(pyridin-3-yloxy)-pyridin-3-yl]-naphthalen-1-yl}-urea;
[4-(6-Morpholin-4-ylmethyl-pyridin-3-yl)-naphthalen-1-yl]-carbamic acid 3-tert-butyl-phenyl ester and
N-(5-tert-Butyl-2-methoxy-3-{3-[4-(6-morpholin-4-ylmethyl-pyridin-3-yl)-naphthalen-1-yl]-ureido}-phenyl)-methanesulfonamide and
or the pharmaceutically acceptable salts thereof.

11. A method of treating chronic obstructive pulmonary disease
said method comprising administering to a patient in need of such treatment a therapeutically effective amount of a compound chosen from:

1-(5-tert-Butyl-2-methylsulfanyl-pyridin-3-yl)-3-[4-(6-morpholin-4-ylmethyl-pyridin-3-yl)-naphthalen-1-yl]-urea;

1-(5-tert-Butyl-2-chloro-pyridin-3-yl)-3-[4-(6-morpholin-4-ylmethyl-pyridin-3-yl)-naphthalen-1-yl]-urea;

1-(5-tert-Butyl-2-methylamino-pyridin-3-yl)-3-[4-(6-morpholin-4-ylmethyl-pyridin-3-yl)-naphthalen-1-yl]-urea;

N-(5-tert-Butyl-3-{3-[4-(6-morpholin-4-ylmethyl-pyridin-3-yl)-naphthalen-1-yl]-ureido}-2-oxo-2H-pyridin-1-yl)-methanesulfonamide;

5-tert-Butyl-7-{3-[4-(6-morpholin-4-ylmethyl-pyridin-3-yl)-naphthalen-1-yl]-ureido}-benzooxazole-2-carboxylic acid amide;

2-(5-tert-Butyl-7-{3-[4-(6-morpholin-4-ylmethyl-pyridin-3-yl)-naphthalen-1-yl]-ureido}-benzooxazol-2-yl)-acetamide;

5-tert-Butyl-2-methoxy-3-{3-[4-(6-morpholin-4-ylmethyl-pyridin-3-yl)-naphthalen-1-yl]-ureido}-benzamide;

N-(5-tert-Butyl-2-methoxy-3-{3-[4-(6-morpholin-4-ylmethyl-pyridin-3-yl)-naphthalen-1-yl]-ureido}-phenyl)-methanesulfonamide;

1-(3-Amino-5-tert-butyl-2-methoxy-phenyl)-3-[4-(6-morpholin-4-ylmethyl-pyridin-3-yl)-naphthalen-1-yl]-urea and 1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea or the pharmaceutically acceptable salts thereof.

* * * * *